(12) United States Patent
Schnaubelt et al.

(10) Patent No.: US 8,288,531 B2
(45) Date of Patent: Oct. 16, 2012

(54) PREPARATION PROCESS

(75) Inventors: Juergen Schnaubelt, Oberhoefen/Warthausen (DE); Thomas Fachinger, Niederheimbach (DE); Michael Konrad, Biberach (DE); Thomas Krueger, Kisslegg (DE); Joern Merten, Gau Algesheim (DE); Carsten Reichel, Rheinboellen (DE); Svenja Renner, Eckenroth (DE); Rolf Schmid, Baltringen (DE); Emanuel Stehle, Ravensburg (DE); Bianca Werner, Mainz (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 222 days.

(21) Appl. No.: 12/672,098

(22) PCT Filed: Aug. 12, 2008

(86) PCT No.: PCT/EP2008/060560
§ 371 (c)(1),
(2), (4) Date: Apr. 15, 2010

(87) PCT Pub. No.: WO2009/021943
PCT Pub. Date: Feb. 19, 2009

(65) Prior Publication Data
US 2011/0087021 A1     Apr. 14, 2011

(30) Foreign Application Priority Data
Aug. 13, 2007  (DE) .......................... 10 2007 038 251

(51) Int. Cl.
| C07D 401/14 | (2006.01) |
| C07D 211/58 | (2006.01) |
| C07D 309/12 | (2006.01) |
| C07C 69/96  | (2006.01) |

(52) U.S. Cl. ........... 540/500; 546/184; 549/416; 560/85
(58) Field of Classification Search ................. 540/500; 546/184; 549/416; 560/85
See application file for complete search history.

(56) References Cited

U.S. PATENT DOCUMENTS 6,809,110 B2 * 10/2004 Binggeli et al. ............ 514/365
2007/0149804 A1   6/2007 Woltering et al.

FOREIGN PATENT DOCUMENTS

| CA | 2600909 A1 | 9/2006 |
| EP | 1801093 A1 | 6/2007 |
| WO | 2006100009 A1 | 9/2006 |

OTHER PUBLICATIONS

Freifelder et al.; Reductions with Ruthenium. Its Use in the Hydrogenation of Pyridines; The Journal of Organic Chemistry; American Chemical Society; vol. 26; No. 10; pp. 3805-3808, (1961).
Ting et al.; Synthesis of substituted 4(Z)-(methoxyimino)pentyl-1-piperidines as dual NK1/NK2 inhibitors; BioOrganic & medicinal Chemistry Letters; Jan. 2001; vol. 11; No. 1; pp. 491-494.
International Search Report, Form PCT/ISA/210, for corresponding PCT/EP2008/060560; date of mailing: Jan. 30, 2009.

* cited by examiner

*Primary Examiner* — Bruck Kifle
(74) *Attorney, Agent, or Firm* — Michael P. Morris; Alan R. Stempel

(57) ABSTRACT

A process for preparing compounds of the formula (I)

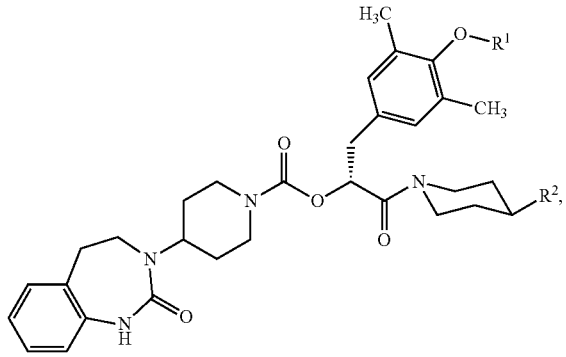

in which $R^1$ and $R^2$ are as defined in the description.

13 Claims, No Drawings

PREPARATION PROCESS

This application is a national stage entry under 35 U.S.C. 371 of international application PCT/EP2008/060560, filed Aug. 12, 2008, which claims priority to German Application No. DE102007038251.2, filed Aug. 13, 2007, each of which is hereby incorporated by reference in its entirety.

The present invention relates to a process for preparing compounds of general formula I

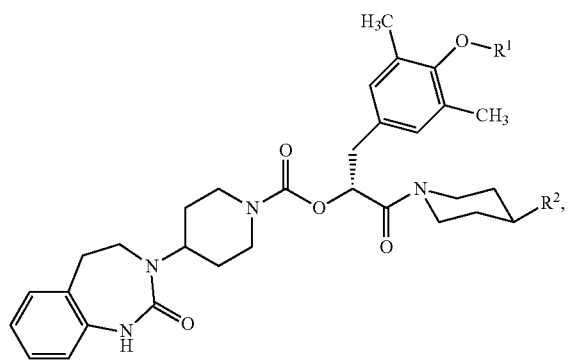

(I)

wherein $R^1$ and $R^2$ are defined as in claim 1, the pharmaceutically acceptable salts thereof and the solvates thereof.

BACKGROUND TO THE INVENTION

Technical Field

The present invention relates to a technical process for preparing compounds of general formula I which have CGRP-antagonistic properties. In addition, the invention relates to the compounds of general formulae V and VI per se, as they are particularly suitable for preparing the compounds of general formula I.

DETAILED DESCRIPTION OF THE INVENTION

The compounds of general formulae V and VI are valuable starting materials for synthesising the compounds of general formula I which have CGRP-antagonistic properties.

The isolated intermediate stages are obtained as crystalline solids, which is of great advantage for the purification and separation of any mixtures of enantiomers that may occur.

In a first aspect the present invention relates to a process for preparing compounds of general formula I

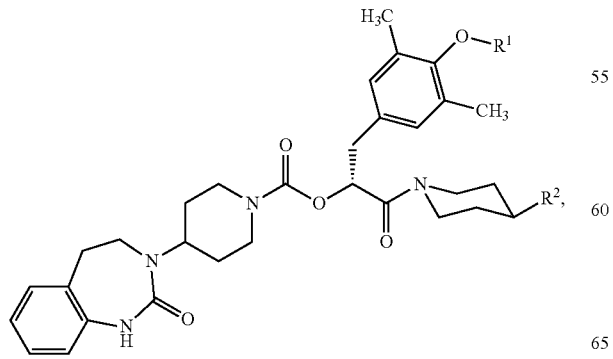

(I)

wherein $R^1$ denotes H, $C_{1-3}$-alkyl, C(O)—O-benzyl, C(O)—O-tert-butyl or benzyl, preferably H or benzyl, and $R^2$ denotes a secondary amine —$NR^{2.1}R^{2.2}$, wherein $R^{2.1}$ and $R^{2.2}$ independently of one another may be selected from among $C_{1-3}$-alkyl and benzyl, or the group —$NR^{2.1}R^{2.2}$ together forms a cyclic amine which may be selected from among morpholin-4-yl, 1-methylpiperazin-4-yl, 1-benzylpiperazin-4-yl, 1-($C_{1-3}$-alkyl-carbonyl)-piperazin-4-yl, 1-(tert-butyloxycarbonyl)-piperazin-4-yl, 1-(benzyloxycarbonyl)-piperazin-4-yl, piperidin-1-yl and pyrrolidin-1-yl, preferably morpholin-4-yl, the salts and solvates thereof, comprising the steps of:

(a) reacting an ethyl glycolate of general formula II

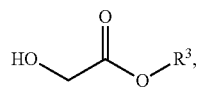

(II)

wherein $R^3$ denotes a $C_{1-6}$-alkyl group, preferably an ethyl group, with a reagent in order to introduce a protective group, preferably 3,4-dihydro-2H-pyran or benzyl chloride, optionally in the presence of an acid and in a non-polar aprotic solvent, to form an ester of general formula III

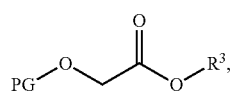

(III)

wherein

PG denotes a protective group, preferably a group selected from

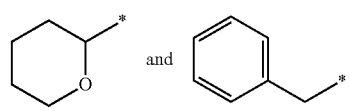

and $R^3$ denotes a $C_{1-6}$-alkyl group, preferably an ethyl group;

(b) mixing an ester of general formula III obtained under (a) with a solvent and reacting in the presence of a strong base with a compound of general formula IV

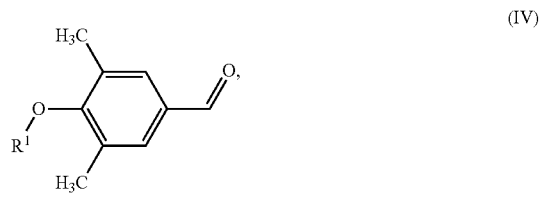

(IV)

wherein $R^1$ is as hereinbefore defined;
(c) mixing a compound of general formula V

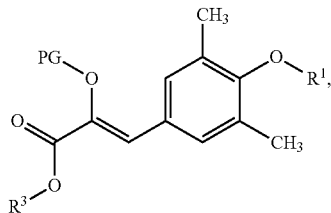
(V)

obtained under (b), wherein PG, $R^1$ and $R^3$ are as hereinbefore defined, with a solvent and adding a strong base;
(d) optionally recrystallising a compound of general formula VI

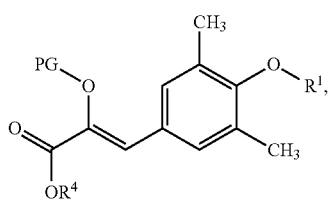
(VI)

obtained under (c)
wherein
PG denotes a protective group, preferably a group selected from

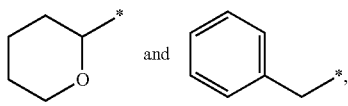

$R^1$ denotes H, $C_{1-3}$-alkyl, C(O)—O-benzyl, C(O)—O-tert-butyl or benzyl, preferably H or benzyl,
$R^4$ denotes a group $H_2N^+(R^{4.1})_2$, $HN^+(R^{4.1})_3$ or $M^+$,
$R^{4.1}$ denotes benzyl, $C_{1-6}$-alkyl or $C_{3-6}$-cycloalkyl, wherein the groups $R^{4.1}$ may be identical or different, and
$M^+$ denotes a metal cation selected from $Na^+$, $K^+$ and $Li^+$, preferably $K^+$, from a polar solvent and isolating the compound obtained;
(e) mixing a compound of general formula VI obtained under (d) with a solvent and adding an acid at low temperature;
(f) cleaving a protective group PG from a compound of general formula VII

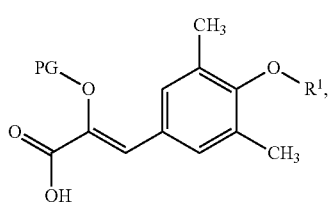
(VII)

obtained under (e), wherein PG and $R^1$ are as hereinbefore defined;
(g) reducing a compound of general formula VIII

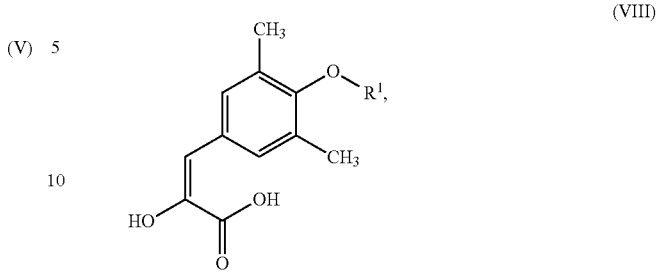
(VIII)

obtained under (f), wherein $R^1$ is as hereinbefore defined, in the presence of a reducing agent and optionally also in the presence of a base, to form a compound of general formula IX

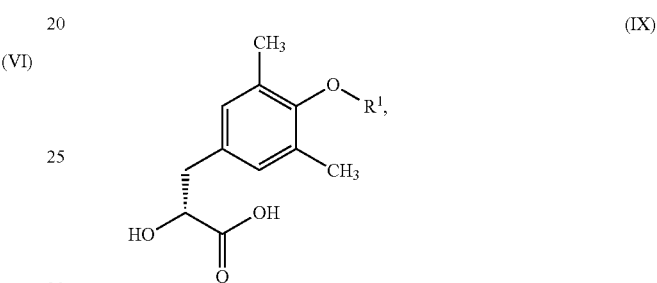
(IX)

wherein $R^1$ is as hereinbefore defined;
(h) isolating a compound of general formula IX, obtained under (g), in the form of an alkali metal salt of general formula X

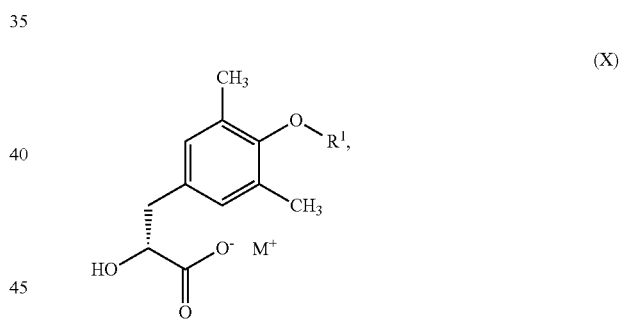
(X)

wherein $R^1$ is as hereinbefore defined and $M^+$ denotes a metal cation selected from among $Li^+$, $Na^+$ and $K^+$, preferably $Na^+$, by adding a corresponding alkaline solution which is selected from among lithium hydroxide, sodium hydroxide and potassium hydroxide;
(i) coupling a compound of general formula X obtained under (h) with a compound of general formula XI

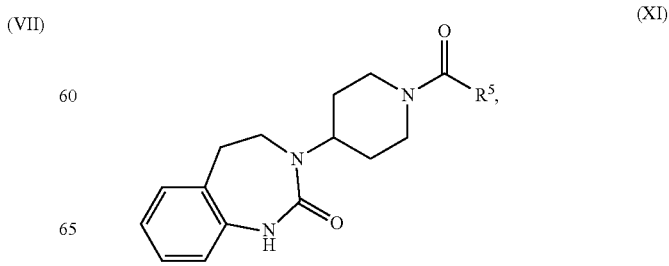
(XI)

wherein R⁵ denotes an imidazole or triazole group, preferably an imidazole group, which is attached via a nitrogen atom;

(j) reacting a product of general formula XII formed in step (i)

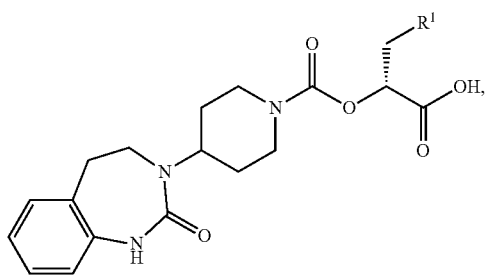

(XII)

wherein R¹ is as hereinbefore defined, with a compound of general formulae XIII

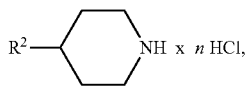

(XIII)

wherein R² is as hereinbefore defined and n denotes one of the numbers 0, 1, 2 or 3;

(k) in order to prepare compounds of general formula I wherein R¹ denotes a hydrogen atom, optionally subsequently cleaving any protective group present from a compound of general formula I wherein R¹ denotes C(O)—O-benzyl, C(O)—O-tert-butyl or a benzyl group; and (l) optionally reacting a compound of general formula I obtained under (k), wherein R¹ denotes a hydrogen atom, with a physiologically acceptable acid in a polar solvent to form a corresponding salt, crystallising out and isolating the corresponding salt.

By a protective group PG mentioned hereinbefore is generally meant a protective group for a hydroxy function. Examples of protective groups for a hydroxy group are the trimethylsilyl, trimethylsilylethyl, tert-butyldimethylsilyl, methoxymethyl, 2-methoxethoxymethyl, tert-butyloxycarbonyl, acetyl, benzoyl, methyl, ethyl, tert-butyl, trityl, benzyl or tetrahydropyranyl.

In the reaction in step (a) 1.0 equivalents of ethyl glycolate may be reacted with 1.0 to 1.3 equivalents of a reagent for introducing a protective group, for example 3,4-dihydro-2H-pyran or benzyl chloride. The aprotic solvent may be selected from among methylene chloride, toluene, o-xylene, m-xylene and p-xylene as well as corresponding mixtures of these solvents. In another embodiment, 0.1 to 0.5 L solvent may be used per mol of ethyl glycolate used.

The acid used in step (a) may be selected from among p-toluenesulphonic acid, methanesulphonic acid, sulphuric acid and benzenesulphonic acid.

The reaction in step (b) may be carried out in a solvent which is selected from among tetrahydrofuran, 2-methyltetrahydrofuran, toluene, tert-butylmethylether, dioxane, mono-, di-, tri- and polyethyleneglycolether. The strong base used in the reaction may be selected from among potassium-tert-butoxide, potassium-tert-amylate, sodium-tert-butoxide, sodium-tert-amylate and lithium-tert-butoxide. In the reaction in step (b), 1.0 equivalents of a compound of general formula IV may be reacted with 0.5 to 2.0 equivalents of a compound of general formula III. In another embodiment 0.5 to 1.0 L solvent are used per mol of compound of general formula IV.

The reaction described hereinbefore under step (c) may be carried out in methanol, ethanol, propanol, isopropanol, tert-amylalcohol or tert-butanol or in a mixture of these solvents. 1.0 to 2.0 L solvent may be used per mol of compound of general formula VI.

The strong inorganic base may be selected from among lithium hydroxide, potassium hydroxide and sodium hydroxide. Preferably the base is added in an amount of from 1.0 to 1.2 mol per mol of compound of general formula V used.

The reaction described hereinbefore under step (e) may be carried out in toluene, tert-butylmethylether, dioxane, tetrahydrofuran or 2-methyltetrahydrofuran as solvent. 1.5 to 5.0 L solvent may be used per mol of compound of general formula VI.

The acid used may be selected from among hydrochloric acid, hydrobromic acid, hydriodic acid, phosphoric acid, p-toluenesulphonic acid, methanesulphonic acid, sulphuric acid and benzenesulphonic acid; hydrochloric acid and methanesulphonic acid are of particular importance according to the invention. 1.5 to 4.0 equivalents of acid are added per mol of compound of general formula VI used.

The reaction may be carried out at a temperature of −20 to 25° C.

The cleaving of the protective group PG mentioned hereinbefore under step (f) may be carried out using methods known from the literature, as described for example in "Protective Groups in Organic Synthesis" (Theodora W. Greene, Peter G. M. Wuts, Third Edition, Wiley Interscience). For example, the cleaving of the protective group PG described hereinbefore under step (f) may be carried out in toluene, tert-butylmethylether, dioxane, tetrahydrofuran or 2-methyltetrahydrofuran as solvent. 1.5 to 5.0 L of solvent of general formula VII may be used.

The acid used may for example be selected from among hydrochloric acid, hydrobromic acid, hydriodic acid, phosphoric acid, p-toluenesulphonic acid, methanesulphonic acid, sulphuric acid and benzenesulphonic acid; hydrochloric acid and methanesulphonic acid are of particular importance according to the invention. 1.5 to 4.0 equivalents of acid may be added per mol of compound of general formula VII used.

The reaction may be carried out at a temperature of −20 to 25° C.

In another embodiment the cleaving of the protective group PG mentioned hereinbefore under step (f) may be carried out in dioxane or toluene as solvent and with the addition of hydrochloric acid.

The base mentioned hereinbefore under step (g) may be selected from among triethylamine, diisopropylethylamine, N-methylmorpholine, N-methylpyrrolidine and pyridine. 2.0 to 2.6 equivalents of base may be added per mol of compound of general formula VIII used.

The reducing agent also described under step (g) may be selected from among β-chlorodiisopinocampheylborane, Alpine borane and methyl-CBS-oxazaborolidine. 1.0 to 1.6 equivalents of reducing agent may be added per mol of compound of general formula VIII used.

The isolation of an alkali metal salt described hereinbefore under step (h) is carried out by adding a corresponding inorganic lye. This may be selected from among lithium hydroxide, sodium hydroxide and potassium hydroxide, preferably in the form of an aqueous solution. 1.0. to 1.5 mol of lye may be added per mol of compound of general formula IX used.

In the coupling in step (i) 1.0 equivalents of a compound of general formula X and 1.0 to 1.5 equivalents of a compound of general formula XI may be suspended in a polar solvent and reacted at elevated temperature in the presence of a strong base.

Polar solvents that may be used according to the invention are tert-butanol, tert-amylalcohol, dimethylformamide, N-methylpyrrolidone or tetrahydrofuran. Preferably 3.0 to 6.0 L solvent are used per mol of the compound of general formula X used.

The base used may be selected from among potassium-tert-butoxide, sodium-tert-butoxide, lithium-tert-butoxide, potassium-tert-amylate and sodium-tert-amylate. The reaction may be carried out at a temperature between 40 and 90° C.

The reaction described hereinbefore under step (j) may be carried out at low temperature in the presence of an amine and a condensing agent in a polar aprotic solvent. Preferably, 1.0 to 1.5 equivalents of a compound of general formula XIII are used per mol of the compound of general formula XII put in.

The amine used may be selected from among triethylamine, diisopropylethylamine, ethyldiisopropylamine and tributylamine. It may be used in an amount of 4.0 to 6.0 equivalents per mol of the compound of general formula XII used.

The condensing agent may be selected from among propanephosphonic anhydride, dicyclohexylcarbodiimide, carbonyldiimidazole, carbonylditriazole, 2-(1H-benzotriazol-1-yl)-1,1,3,3-tetramethyluronium-tetrafluoroborate, 1-ethyl-3-(3'-dimethylamino-propyl)-carbodiimide and chlorodimethoxy-triazine, optionally in the presence of hydroxysuccinimide, hydroxybenzotriazole, p-nitrophenol or pentafluorophenol. It is preferably used in an amount of 1.5 to 2.0 equivalents per mol of the compound of general formula XII used.

Tetrahydrofuran, 2-methyltetrahydrofuran, toluene or ethyl acetate may be used as the polar aprotic solvent. It is preferably used in an amount of 4.0 to 6.0 L per mol of compound of general formula XII used.

Preferably, according to the invention, the reaction is carried out at a temperature between 0 and 50° C.

For the optional cleaving of a protective group in step (k), a compound of general formula I obtained in step (j) wherein $R^1$ denotes C(O)—O-benzyl or a benzyl group is dissolved in a polar solvent, such as for example methanol, ethanol, water, acetone, tetrahydrofuran, dimethylformamide, toluene or propanol, and hydrogenated in a pressurised reactor. The hydrogenation agent used may be for example Pd/C or Pd(OH)$_2$. Advantageous conditions for the hydrogenation are temperatures of 40 to 80° C. and an excess hydrogen pressure of not more than 3 bar. After the catalyst has been filtered off the compound of general formula I wherein $R^1$ denotes a hydrogen atom may be obtained by concentrating the solvent with the addition of another polar solvent, preferably ethanol.

The reaction described hereinbefore under step (l) may take place in methanol, ethanol, propanol, isopropanol or water or in a mixture of these solvents. The physiologically acceptable acid may be selected from among hydrobromic acid, phosphoric acid, nitric acid, hydrochloric acid, sulphuric acid, methanesulphonic acid, ethanesulphonic acid, benzenesulphonic acid, p-toluenesulphonic acid, malic acid, succinic acid, acetic acid, fumaric acid, maleic acid, mandelic acid, lactic acid, tartaric acid and citric acid.

The compounds of general formula XI

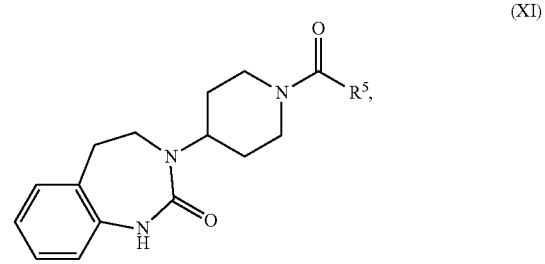

(XI)

wherein $R^5$ denotes an imidazole or triazole group, preferably an imidazole group which is bound via a nitrogen atom, are prepared by a process comprising the steps of:

(a) dissolving carbonyldiimidazole or carbonylditriazole, preferably carbonyldiimidazole, in a polar aprotic solvent and reacting at elevated temperature with 1,3,4,5-tetrahydro-3-(4-piperidinyl)-2H-1,3-benzodiazepin-2-one; and (b) crystallising out a crude product obtained in step (a) by adding another polar aprotic solvent, if $R^5$ denotes an imidazole group.

The solvent mentioned hereinbefore under step (a) may be selected from among acetone, acetonitrile, tert-butylmethylether, N,N-dimethylacetamide, dimethylformamide, dimethylsulphoxide, pyridine and N-methylpyrrolidone.

The polar, aprotic solvent mentioned hereinbefore under step (b) may be selected from among tert-butylmethylether, dimethylformamide, tetrahydrofuran, toluene and 2-methyltetrahydrofuran.

A method of preparing 1,3,4,5-tetrahydro-3-(4-piperidinyl)-2H-1,3-benzodiazepin-2-one is described in European Patent Application No. 04017424.5.

In a second aspect the invention relates to the compounds of general formula V

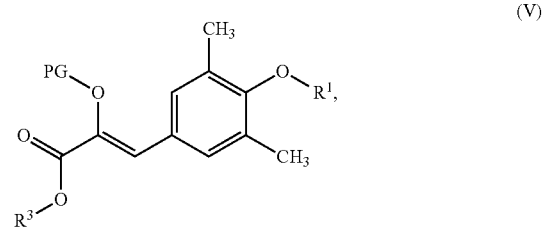

(V)

wherein

PG denotes a protective group, preferably a group selected from

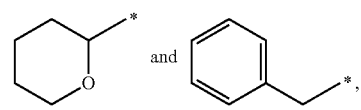

$R^1$ denotes H, $C_{1-3}$-alkyl, C(O)—O-benzyl, C(O)—O-tert-butyl or benzyl, preferably benzyl, and $R^3$ denotes $C_{1-6}$-alkyl, preferably ethyl.

A preferred second aspect encompasses the following compounds of formulae Va to Vd:

| No. | Structure |
|---|---|
| (1) | (Va) |
| (2) | (Vb) |
| (3) | (Vc) |
| (4) | (Vd) |

A more preferred second aspect relates to the compound ethyl (3Z)-3-(4-benzyloxy-3,5-dimethyl-phenyl)-2-tetrahydropyran-2-yloxy)-acrylate of formula Va

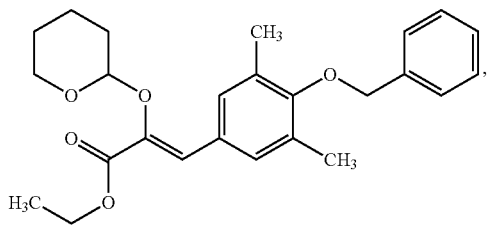

(Va)

which occurs in crystalline form and is characterised by a high degree of stability.

The crystalline compound of formula Va is characterised by a characteristic melting point of T=123±3° C. The value given was determined by Differential Scanning Calorimetry (DSC: evaluated by Onset, heating rate: 10° C./min) (Netzsch STA Jupiter).

A further object of the present invention relates to the use of the above-mentioned compounds of general formula V as intermediate products for preparing compounds of general formula I according to a process described hereinbefore under the first embodiment.

In a third aspect the present invention relates to a process for preparing compounds of general formula V

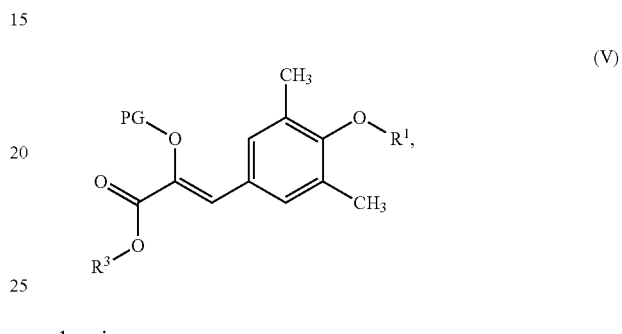

(V)

wherein

PG denotes a protective group, preferably a group selected from

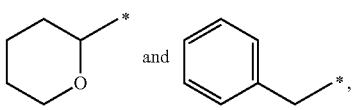

$R^1$ denotes H, $C_{1-3}$-alkyl, C(O)—O-benzyl, C(O)—O-tert-butyl or benzyl, preferably benzyl, and $R^3$ denotes $C_{1-6}$-alkyl, preferably ethyl, characterised in that (a) a glycolic acid ester of general formula II

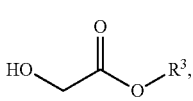

(II)

wherein $R^3$ denotes a $C_{1-6}$-alkyl group, preferably an ethyl group, is reacted with a reagent for introducing a protective group, preferably 3,4-dihydro-2H-pyran, benzyltrichloroacetimidate or a benzyl halide, optionally in the presence of an acid or a base, in a non-polar aprotic solvent to form an ester of general formula III

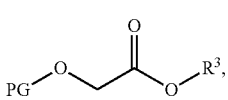

(III)

wherein

PG denotes a protective group, preferably a group selected from

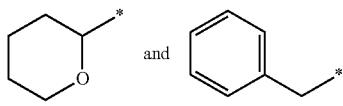

and $R^3$ denotes a $C_{1-6}$-alkyl group, preferably an ethyl group;

(b) an ester of general formula III obtained under (a) is mixed with a solvent and reacted in the presence of a strong base with a compound of general formula IV

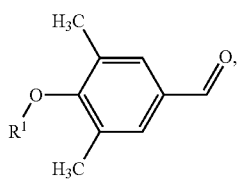

(IV)

wherein $R^1$ is as hereinbefore defined, and (c) a compound of general formula V

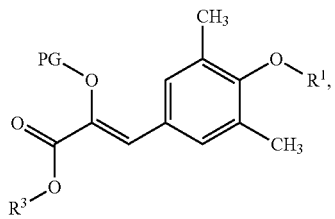

(V)

obtained under (b) in this way, wherein PG, $R^1$ and $R^3$ are as hereinbefore defined, is optionally recrystallised.

In the reaction in step (a) 1.0 equivalents of ethyl glycolate may be reacted with 1.0 to 1.1 equivalents of a reagent for introducing a protective group, for example 3,4-dihydro-2H-pyran or benzyl chloride. The non-polar aprotic solvent may be selected from among toluene, o-xylene, m-xylene and p-xylene as well as corresponding mixtures of these solvents. 0.1 to 0.5 L solvent may be used per mol of ethyl glycolate used.

The benzyl halide used in step (a) may be selected from among benzyl chloride, benzyl bromide and benzyl iodide.

The acid used in step (a) may be selected from among p-toluenesulphonic acid, methanesulphonic acid, sulphuric acid and benzenesulphonic acid.

The base used in step (a) may be selected from among inorganic bases or organic bases. Suitable inorganic bases are alkali metal hydroxides, e.g. sodium hydroxide or potassium hydroxide, or silver oxide. Inorganic bases that may be used are tertiary amines, e.g. triethylamine or Hünig base.

The reaction in step (b) may be carried out in a solvent which is selected from among 2-methyltetrahydrofuran, toluene, tetrahydrofuran, tert-butylmethylether, dioxane, mono-, di-, tri- and polyethyleneglycolether. The strong base used in the reaction may be selected from among 1,4-diazabicyclo[2,2,2]octane (DABCO), potassium-tert-butoxide, potassium-tert-amylate, sodium-tert-butoxide, sodium-tert-amylate and lithium-tert-butoxide.

If the compounds of general formula V are crystalline, they may be recrystallised as described hereinbefore under step (c).

In a fourth aspect the present invention relates to the compounds of general formula VI

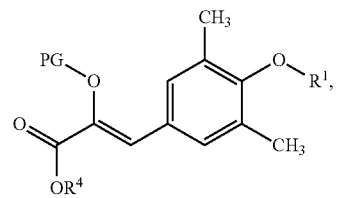

(VI)

wherein

PG denotes a protective group, preferably a group selected from

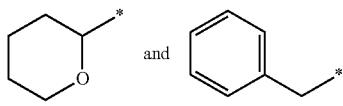

$R^1$ denotes H, $C_{1-3}$-alkyl, C(O)—O-benzyl, C(O)—O-tert-butyl or benzyl, preferably benzyl, $R^4$ denotes a group $H_2N^+(R^{4.1})_2$, $HN^+(R^{4.1})_3$ or $M^+$, $R^{4.1}$ denotes benzyl, $C_{1-6}$-alkyl or $C_{3-6}$-cycloalkyl and $M^+$ denotes a metal cation selected from $Na^+$, $K^+$ and $Li^+$, preferably $K^+$.

A preferred fourth aspect encompasses the following compounds of formulae VIa to VId:

| No. | Structure |
|---|---|
| (1) | (VIa) |
| (2) | (VIb) |

| No. | Structure |
|---|---|
| (3) | 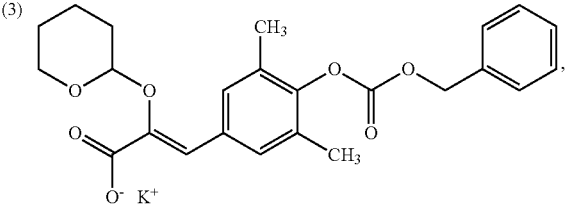 (VIc) |
| (4) | 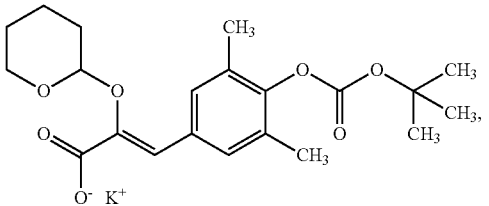 (VId) |
| (5) | 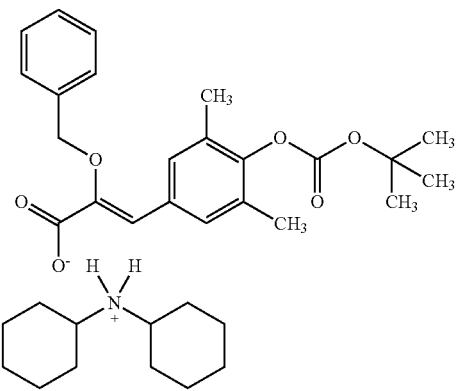 (VIe) | and optionally the hydrates thereof.

A more preferred fourth aspect relates to the compound (3Z)-3-(4-benzyloxy-3,5-dimethyl-phenyl)-2-tetrahydro-pyran-2-yloxy)-acrylic acid-monopotassium salt of formula VIa

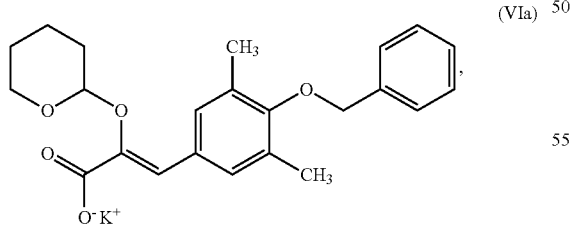

(VIa)

which occurs in crystalline form and is characterised by a high degree of stability.

The crystalline compound of formula VIa is characterised by a characteristic melting point of T=89±3° C. The value stated was determined by Differential Scanning Calorimetry (DSC: evaluated by Onset, heating rate: 10° C./min) (Netzsch STA Jupiter).

A more preferred fourth aspect relates to the compound (3Z)-3-(4-tert-butyl-oxycarbonyloxy-3,5-dimethyl-phenyl)-2-tetrahydro-pyran-2-yloxy)-acrylic acid monodicyclohexylamine salt of formula VIe

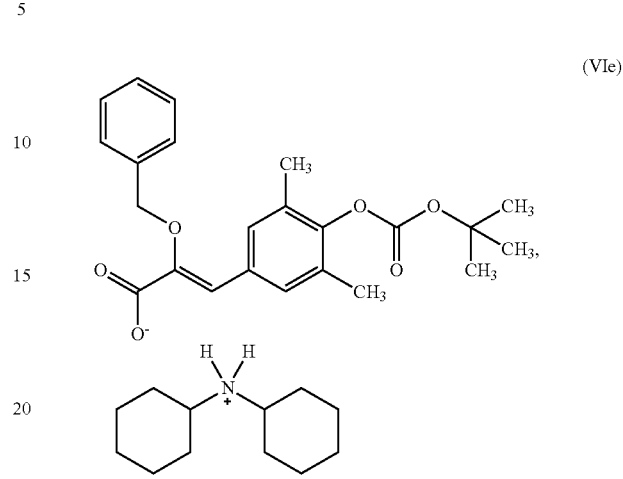

(VIe)

which occurs in crystalline form and is characterised by a high degree of stability.

The crystalline compound of formula VIe is characterised by a characteristic melting point of T=140±3° C. The value stated was determined by Differential Scanning Calorimetry (DSC: evaluated by Onset, heating rate: 10° C./min) (Netzsch STA Jupiter).

A further object of the present invention relates to the use of the above-mentioned compounds of general formula VI as intermediate products for preparing compounds of general formula I according to a process described hereinbefore under the first embodiment.

In a fifth aspect the present invention relates to a process for preparing compounds of general formula VI

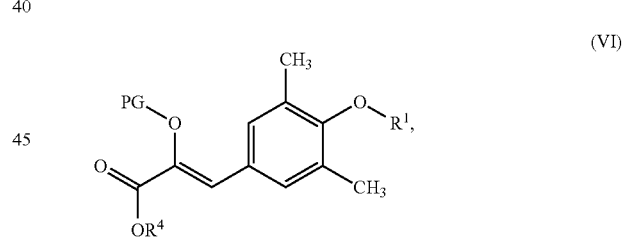

(VI)

wherein

PG denotes a protective group, preferably a group selected from

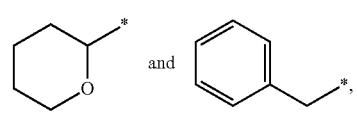

$R^1$ denotes H, $C_{1-3}$-alkyl, C(O)—O-benzyl, C(O)—O-tert-butyl or benzyl, preferably benzyl, $R^4$ denotes a group $H_2N^+(R^{4.1})_2$, $HN^+(R^{4.1})_3$ or $M^+$, $R^{4.1}$ denotes benzyl, $C_{1-6}$-alkyl or $C_{3-6}$-cycloalkyl and $M^+$ denotes a metal cation selected from $Na^+$, $K^+$ and $Li^+$, preferably $K^+$, characterised in that (a) a compound of general formula V

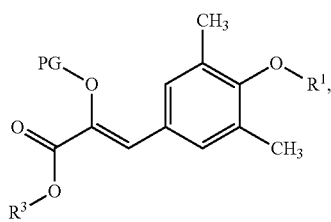

wherein PG, $R^1$ and $R^3$ are as hereinbefore defined, is mixed with a polar solvent and a strong inorganic base is added; and (b) a compound of general formula VI

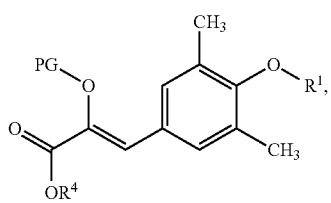

obtained under (a), wherein PG, $R^1$ and $R^4$ are as hereinbefore defined, is then isolated.

The reaction described hereinbefore under step (a) may be carried out in methanol, ethanol, propanol, isopropanol, tert-amylalcohol or tert-butanol or in a mixture of these polar solvents.

The strong inorganic base may be selected from among lithium hydroxide, potassium hydroxide and sodium hydroxide.

A starting compound of general formula V is prepared as described hereinbefore under the third embodiment.

In a sixth aspect the present invention relates to a process for preparing compounds of general formula XIII

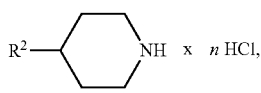

wherein
n denotes one of the numbers 1, 2 or 3 and
$R^2$ denotes a secondary amine $—NR^{2.1}R^{2.2}$, wherein
$R^{2.1}$ and $R^{2.2}$ independently of one another may be selected from among $C_{1-3}$-alkyl and benzyl, or
the group $—NR^{2.1}R^{2.2}$ together forms a cyclic amine which may be selected from among morpholin-4-yl, 1-methylpiperazin-4-yl, 1-benzylpiperazin-4-yl, 1-($C_{1-3}$-alkyl-carbonyl)-piperazin-4-yl, 1-(tert-butyloxycarbonyl)-piperazin-4-yl, 1-(benzyloxycarbonyl)piperazin-4-yl, piperidin-1-yl and pyrrolidin-1-yl, preferably morpholin-4-yl,
comprising the steps of:

(a) reacting 1-benzylpiperidone with an amine of general formula XIV

wherein $R^{2.1}$ and $R^{2.2}$ are as hereinbefore defined, in a solvent, cleaving water;

(b) reducing the enamine formed in (a) under pressure and in the presence of a catalyst and isolating the resulting product of general formula XV

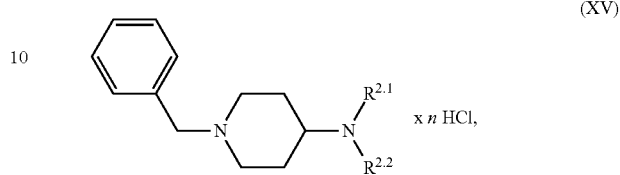

wherein n, $R^{2.1}$ and $R^{2.2}$ are as hereinbefore defined, by the addition of hydrochloric acid;

(c) eliminating the benzyl protective group from a compound of general formula XV obtained under (b) and isolating a compound of general formula XVI

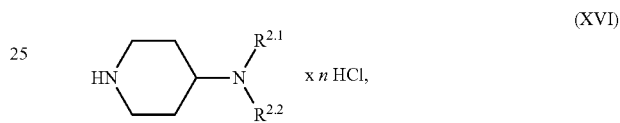

wherein n, $R^{2.1}$ and $R^{2.2}$ are as hereinbefore defined.

In the reaction in step (a) 1.0 equivalents of 1-benzylpiperidone may be reacted with 1.8 to 2.2 equivalents, preferably 2.0 equivalents, of an amine of general formula XIV.

The solvent used may be selected from among ethyl acetate, isopropylacetate, toluene and methyltetrahydrofuran, of which isopropylacetate is preferably used. Preferably 0.5 to 1.0 L of solvent are used per mol of 1-benzylpiperidone.

The reduction in step (b) is carried out in the presence of a catalyst which may be selected from among Raney nickel, platinum/charcoal and platinum dioxide; Raney nickel is preferably used. Advantageous conditions for the hydrogenation are temperatures from 20 to 70° C. and an excess hydrogen pressure of not more than 5 bar. After the catalyst has been filtered off the hydrogenation product may be concentrated by distilling off the solvent.

To isolate a hydrochloride of general formula XV, 2.0 to 2.5 equivalents of hydrochloric acid are added, based on the amount of 1-benzylpiperidone used.

The cleaving of a benzyl protective group from a compound of general formula XV, as described under step (c), may be carried by hydrogenation out in a polar solvent, such as for example methanol, ethanol, propanol, tert-butanol, water, acetone, tetrahydrofuran, dimethylformamide or mixtures of these solvents. The solvent may be added in an amount of 0.5 to 2.5 L per mol of the compound of general formula XV used, preferably 0.7 to 2.2 L per mol of the compound of general formula XV, preferably 0.7 to 1.5 L per mol of the compound of general formula XV, particularly preferably 1.0 L per mol of the compound of general formula XV used. The hydrogenation is carried out in the presence of a catalyst, which may be selected from among palladium/charcoal and palladium hydroxide; preferably, palladium/charcoal is used.

Advantageous conditions for the hydrogenation are temperatures from 40 to 80° C. and an excess hydrogen pressure of at most 5 bar.

A compound of general formula XIII may be isolated for example by crystallisation.

Alternatively a compound of general formula XIII, wherein n and $R^2$ are as hereinbefore defined, may also be prepared by a process comprising the steps of:

(a) reacting 1-benzylpiperidone with an amine of general formula XIV

wherein $R^{2.1}$ and $R^{2.2}$ are as hereinbefore defined, in a solvent, with cleaving of hydrogen;

(b) reducing the enamine obtained in (a) under pressure and in the presence of a catalyst and isolating the resulting product of general formula XV

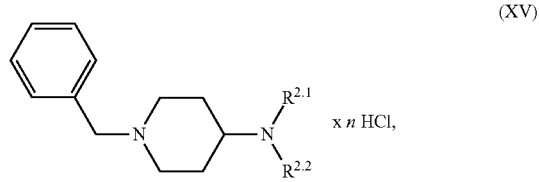

wherein n, $R^{2.1}$ and $R^{2.2}$ are as hereinbefore defined, by the addition of hydrochloric acid;

(c) reacting a compound of general formula XV obtained under (b), wherein n, $R^{2.1}$ and $R^{2.2}$ are as hereinbefore defined, with a base in a polar solvent, thus forming a compound of general formula XV wherein $R^{2.1}$ and $R^{2.2}$ are as hereinbefore defined and n denotes the number 0;

(d) eliminating the benzyl protective group from a compound of general formula XV obtained under (c) and isolating a compound of general formula XVI

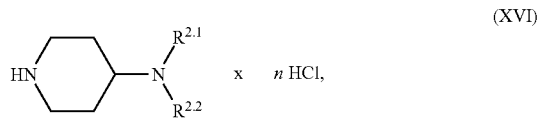

wherein $R^{2.1}$ and $R^{2.2}$ are as hereinbefore defined and n denotes the number 0; and (e) reacting a compound of general formula XVI obtained under (d), wherein n denotes the number 0, by the addition of hydrochloric acid in a solvent, to obtain a compound of general formula XVI, wherein n denotes one of the numbers 1, 2 or 3.

In the reaction in step (a) 1.0 equivalents of 1-benzylpiperidone may be reacted with 1.8 to 2.2 equivalents, preferably 2.0 equivalents, of an amine of general formula XIV.

The solvent used may be selected from among ethyl acetate, isopropyl acetate, toluene and methyltetrahydrofuran, of which isopropyl acetate is preferably used. Preferably 0.5 to 1.0 L of solvent are used per mol of 1-benzylpiperidone.

The reduction in step (b) is carried out in the presence of a catalyst which may be selected from among Raney nickel, platinum/charcoal and platinum dioxide; preferably, Raney nickel is used. Advantageous conditions for the hydrogenation are temperatures of 20 to 70° C. and an excess hydrogen pressure of not more than 5 bar. After the catalyst has been filtered off the hydrogenation product may be concentrated by distilling off the solvent.

To isolate a hydrochloride of general formula XV, 2.0 to 2.5 equivalents hydrochloric acid are added, based on the amount of 1-benzylpiperidone used.

The reaction described in step (c) may be carried out in a polar solvent selected from among methanol, ethanol, propanol, isopropanol, butanol, water, tert-butanol or mixtures of these solvents. The solvent may be used in an amount from 1.0 to 3.0 L/mol of the compound of general formula XV used.

The base used may be an alkali metal hydroxide or an alkali metal carbonate, for example sodium hydroxide, potassium hydroxide, sodium carbonate or potassium carbonate.

The cleaving of a benzyl protective group from a compound of general formula XV described under step (d) may be carried out by hydrogenation in a polar solvent, such as for example methanol, ethanol, propanol, tert-butanol, water, acetone, tetrahydrofuran, dimethylformamide or mixtures of these solvents. The solvent may be added in an amount of 0.5 to 2.5 L per mol of the compound of general formula XV used, preferably 0.7 to 1.5 L per mol of the compound of general formula XV used, particularly preferably 1.3 L per mol of the compound of general formula XV used.

The hydrogenation is carried out in the presence of a catalyst which may be selected from among palladium/charcoal and palladium hydroxide; preferably palladium/charcoal is used.

Advantageous conditions for the hydrogenation are temperatures of 40 to 80° C. and an excess hydrogen pressure of not more than 5 bar.

A compound of general formula XIII may be isolated for example by crystallisation.

The reaction described under step (e) to obtain a compound of general formula XVI wherein n denotes the number 1, 2 or 3 is carried out by the addition of 1.8 to 2.5 equivalents, preferably 2.0 to 2.2 equivalents of hydrochloric acid, in each case based on the amount of compound of general formula XVI used, wherein n denotes the number 0.

Methanol or ethanol may be used as solvent. The solvent is added in an amount of 1.0 to 7.0 L per mol of the compound of general formula XVI used, wherein n denotes the number 0.

In another aspect the present invention relates to the use of the compounds of general formula XIII previously mentioned as intermediate products for preparing compounds of general formula I by a process described hereinbefore under the first embodiment.

TERMS AND DEFINITIONS USED

By the term "secondary amine" is meant an amino group of general formula —$NR^{2.1}R^{2.2}$, wherein the groups $R^{2.1}$ and $R^{2.2}$ independently of one another may be selected from among $C_{1-3}$-alkyl and benzyl, or the group —$NR^{2.1}R^{2.2}$ together forms a cyclic amine which may be selected from among morpholin-4-yl, 1-methylpiperazin-4-yl, 1-benzylpiperazin-4-yl, 1-$C_{1-3}$-alkylcarbonyl-piperazin-4-yl, 1-tert-butyloxycarbonyl-piperazin-4-yl, 1-benzyloxycarbonyl-piperazin-4-yl, piperidin-1-yl and pyrrolidin-1-yl.

Examples include:

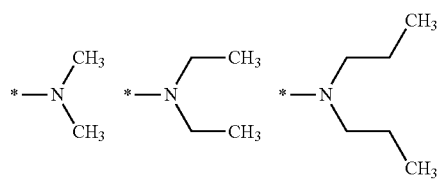

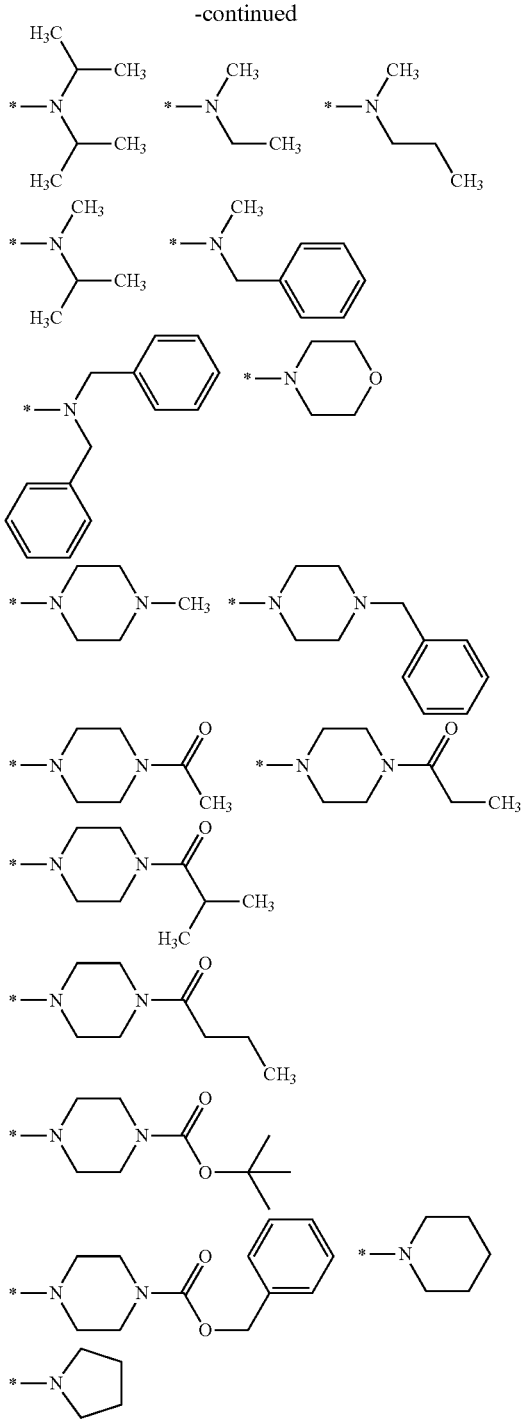

stated, the cyclic alkyl groups may be substituted by one or more groups selected from among methyl, ethyl, iso-propyl, tert-butyl, hydroxy, fluorine, chlorine, bromine and iodine.

The compounds of general formula I may have basic groups such as e.g. Amino functions. They may therefore be present as internal salts, as salts with pharmaceutically useable inorganic acids such as for example hydrobromic acid, phosphoric acid, nitric acid, hydrochloric acid, sulphuric acid, methanesulphonic acid, ethanesulphonic acid, benzenesulphonic acid, p-toluenesulphonic acid or organic acids such as for example malic acid, succinic acid, acetic acid, fumaric acid, maleic acid, mandelic acid, lactic acid, tartaric acid or citric acid.

The invention relates to the respective compounds optionally in the form of the individual optical isomers, mixtures of the individual enantiomers or racemates, in the form of the tautomers as well as in the form of the free bases or the corresponding acid addition salts with pharmacologically acceptable acids.

EXPERIMENTAL SECTION

Example 1.1

Ethyl(tetrahydropyran-2-yloxy)-acetate (B)

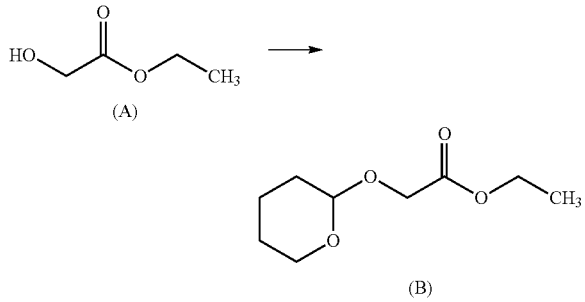

20.00 kg (182.50 mol) ethyl glycolate (A) were dissolved in 60.0 L toluene and 71.04 g (0.366 mol) 4-toluenesulphonic acid monohydrate were added. A solution of 15.83 kg (182.50 mol) 3,4-dihydro-2H-pyran in 40.0 L toluene was added dropwise at 20° C. to the reaction mixture obtained. Then the reaction mixture was stirred for 1 hour at 20° C. and after the reaction had ended 37.0 L water and 3.69 L (49.28 mol) ammonia solution (25%) were added. After phase separation the organic phase was washed with 40.0 L water and then the solvent was completely distilled off in vacuo.

Yield: 32.0 kg (88% of theory)

Example 1.2

Ethyl(tetrahydropyran-2-yloxy)-acetate (B)

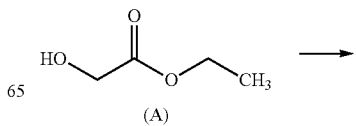

By the term "$C_{1-3}$-alkyl" (including those which are a part of other groups) are meant branched and unbranched alkyl groups with 1 to 3 carbon atoms and by the term "$C_{1-6}$-alkyl" are meant branched and unbranched alkyl groups with 1 to 6 carbon atoms. Examples of these include: methyl, ethyl, n-propyl, iso-propyl, n-butyl, iso-butyl, tert-butyl, n-pentyl, tert-amyl or n-hexyl. The abbreviations Me, Et, n-Pr, i-Pr etc. Are optionally also used for the above-mentioned groups.

By the term "$C_{3-6}$-cycloalkyl" (including those which are a part of other groups) are meant cyclic alkyl groups with 3 to 6 carbon atoms. Examples of these include: cyclopropyl, cyclobutyl, cyclopentyl or cyclohexyl. Unless otherwise -continued

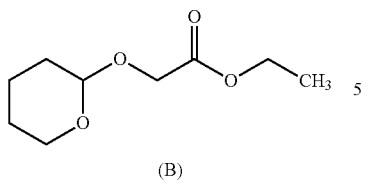

(B)

100.00 kg (960.52 mol) ethyl glycolate (A) were dissolved in 180.0 L toluene and 365.22 g (1.92 mol) 4-toluenesulphonic acid monohydrate were added. At 20° C. a solution of 80.80 kg (960.52 mol) 3,4-dihydro-2H-pyran was added dropwise to the reaction mixture obtained and then the mixture was washed with 20.0 L toluene. The reaction mixture was stirred for 1 hour at 20° C. and after the reaction was complete it was combined with 100.0 L water and 6.53 kg (96.05 mol) ammonia solution (25%). After phase separation the organic phase was washed with 100.0 L water and then the solvent was distilled off completely in vacuo.

Yield: 188.4 kg (94.7% of theory)

Example 2.1

Ethyl(3Z)-3-(4-benzyloxy-3,5-dimethyl-phenyl)-2-tetrahydro-pyran-2-yloxy)-acrylate (D)

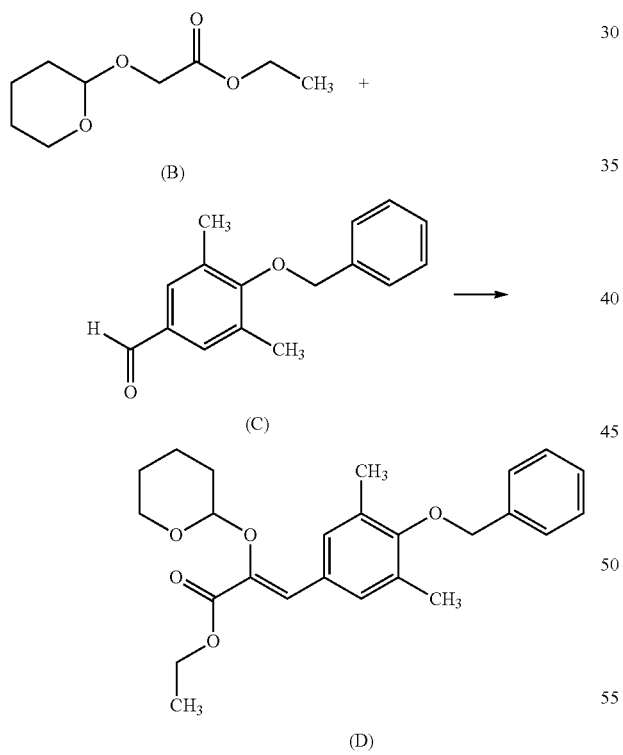

20.00 kg (83.23 mol) 4-benzyloxy-3,5-dimethylbenzaldehyde (C) were dissolved in 50.0 L tetrahydrofuran and 31.68 kg (149.81 mol) ethyl(tetrahydropyran-2-yloxy)-acetate (B) were added. At 20° C. 25.68 kg (91.55 mol) potassium-tert-amylate (45% in tetrahydrofuran) were added dropwise. Then the reaction mixture obtained was stirred for 3.5 hours at 20° C. and after the reaction had ended 120.0 L water was added.

The suspension obtained was cooled to 0° C. and stirred for 1 hour at this temperature. Then the product was removed by centrifuging and dried.

Yield: 25.04 kg (73% of theory)
Chemical purity (HPLC): 99.8%
Melting point: 122.6° C.

Example 2.2

Ethyl(3Z)-3-(4-benzyloxy-3,5-dimethyl-phenyl)-2-tetrahydro-pyran-2-yloxy)-acrylate (D)

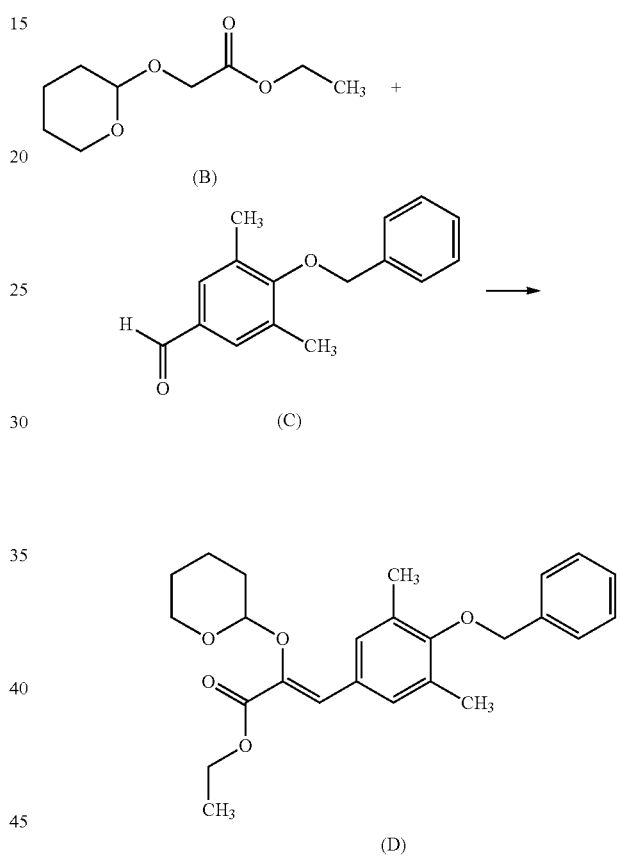

100.0 kg (416.15 mol) 4-benzyloxy-3,5-dimethylbenzaldehyde (C) were dissolved in 200.0 L tetrahydrofuran and 141.41 kg (749.06 mol) ethyl(tetrahydropyran-2-yloxy)-acetate (B) were added. At 20° C., 128.42 kg (457.76 mol) potassium-tert-amylate (45% in tetrahydrofuran) were added dropwise. Then the reaction mixture obtained was stirred for 2 hours at 25° C. and after the reaction was complete 300.0 L water were added. The suspension obtained was stirred for 1 hour at 25° C. Then the product was removed by centrifuging and dried.

Yield: 118.9 kg (69.6% of theory)
Chemical purity (HPLC): 99.8%
Melting point: 122.6° C.

Example 3.1

(3Z)-3-(4-benzyloxy-3,5-dimethyl-phenyl)-2-tetrahydro-pyran-2-yloxy)-acrylic acid monopotassium salt (E)

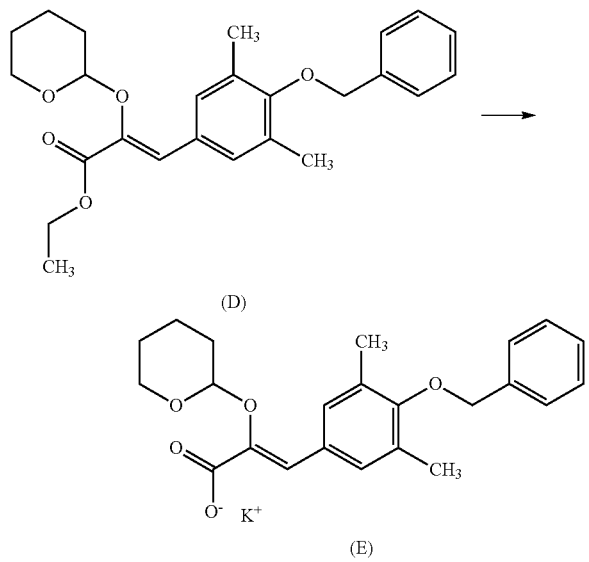

35.00 kg (85.26 mol) ethyl (3Z)-3-(4-benzyloxy-3,5-dimethyl-phenyl)-2-tetrahydro-pyran-2-yloxy)-acrylate (D) were suspended in 157 L tert-butanol and 11.69 kg (93.79 mol) of a 45% potassium hydroxide solution were metered in. After rinsing with 17.5 L tert-butanol the reaction mixture was refluxed and stirred for 1 hour. Then the solution was cooled to 60° C. and 140.0 L tert-butylmethylether were added. The solution was then cooled further and inoculated at 20° C. After 1.5 hours stirring at 20° C. the product obtained was removed by centrifuging and dried.

Yield: 35.50 kg (99% of theory)
Chemical purity (HPLC): 99.8%
Melting point: 89° C.

Example 3.2

(3Z)-3-(4-benzyloxy-3,5-dimethyl-phenyl)-2-tetrahydro-pyran-2-yloxy)-acrylic acid monopotassium salt (E)

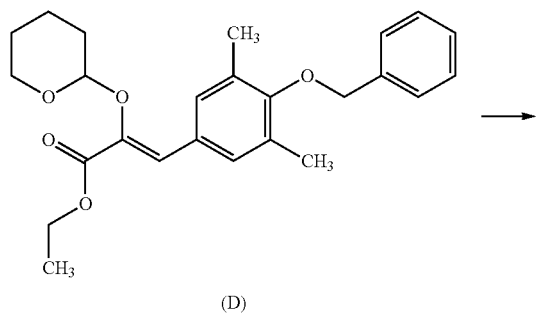

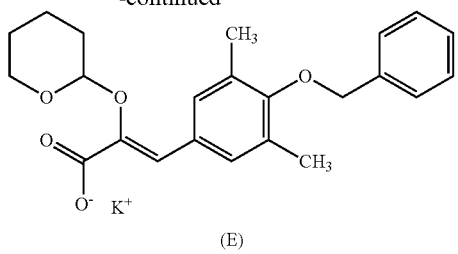

115.0 kg (280.15 mol) ethyl (3Z)-3-(4-benzyloxy-3,5-dimethyl-phenyl)-2-tetrahydro-pyran-2-yloxy)-acrylate (D) were suspended in 430 L tert-amylalcohol and 38.42 kg (308.16 mol) of a 45% potassium hydroxide solution were metered in. After rinsing with 30.0 L tert-amylalcohol the reaction mixture was heated to reflux temperature and stirred for 1 hour. Then the solution was cooled to 60° C. and 230.0 L of tert-butylmethylether were added. The solution was then cooled further and inoculated at 40° C. After 1.0 hours stirring at 20° C. the product obtained was centrifuged off and dried.

Yield: 116.6 kg (99% of theory)
Chemical purity (HPLC): 99.8%
Melting point: 89° C.

Example 4.1

($\alpha$R)-$\alpha$-Hydroxy-3,5-dimethyl-4-(phenylmethoxy)-phenylpropionic acid monosodium salt (H)

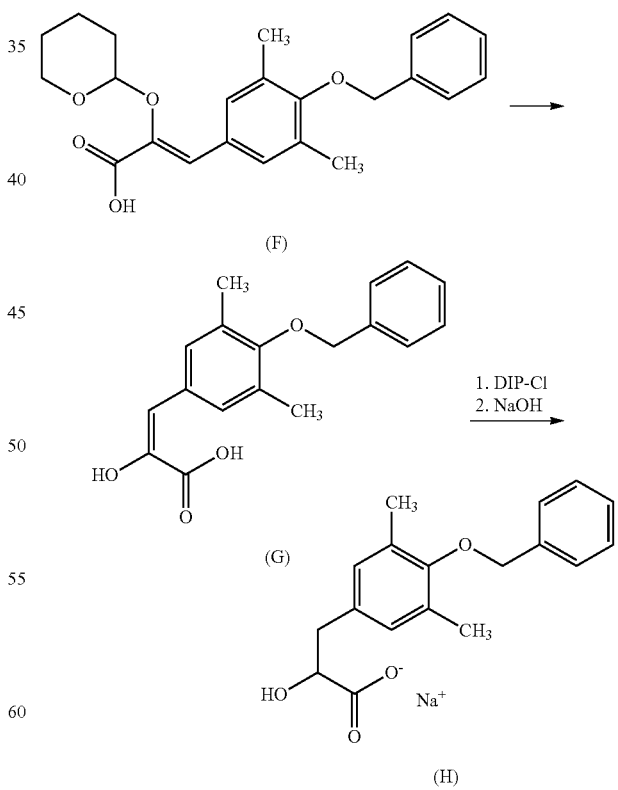

24.00 kg (57.07 mol) of (3Z)-3-(4-benzyloxy-3,5-dimethyl-phenyl)-2-tetrahydro-pyran-2-yloxy)-acrylic acid monopotassium salt (E) were suspended in 240.0 L of 2-methyltetrahydrofuran. 12.07 kg (125.55 mol) methanesulphonic acid were added at 0 to 5° C. The resulting suspension was stirred at 0° C. for 30 minutes. After the solution obtained had been cooled to −15° C., 13.86 kg (136.97 mol) triethylamine were added. The resulting suspension was then combined with 42.24 kg (85.60 mol) with diisopinocampheylborochloride (65% in heptane) at a temperature of −15° C. Then the temperature of the reaction mixture was allowed to rise to 11° C. within 1 hour and 48.0 L of water were added dropwise. The temperature of the 2-phase mixture was adjusted to 25° C. and the aqueous phase was separated off. The organic phase was washed with 48.0 L water. Then 144 L solvent were distilled off in vacuo. The residue obtained was diluted by the addition of 168.0 L tetrahydrofuran and cooled to 3° C. The reaction solution obtained was inoculated at 3° C. and a mixture of 4.79 kg (59.92 mol) sodium hydroxide solution (50%) in 20 L water was metered in. After 45 minutes stirring at 0 to 5° C. the product obtained was removed by centrifuging and dried.

Yield: 9.80 kg (53% of theory)
ee value: 98%
Chemical purity (HPLC): 99.9%

Example 4.2

(αR)-α-hydroxy-3,5-dimethyl-4-(phenylmethoxy)-phenylpropionic acid monosodium salt (H)

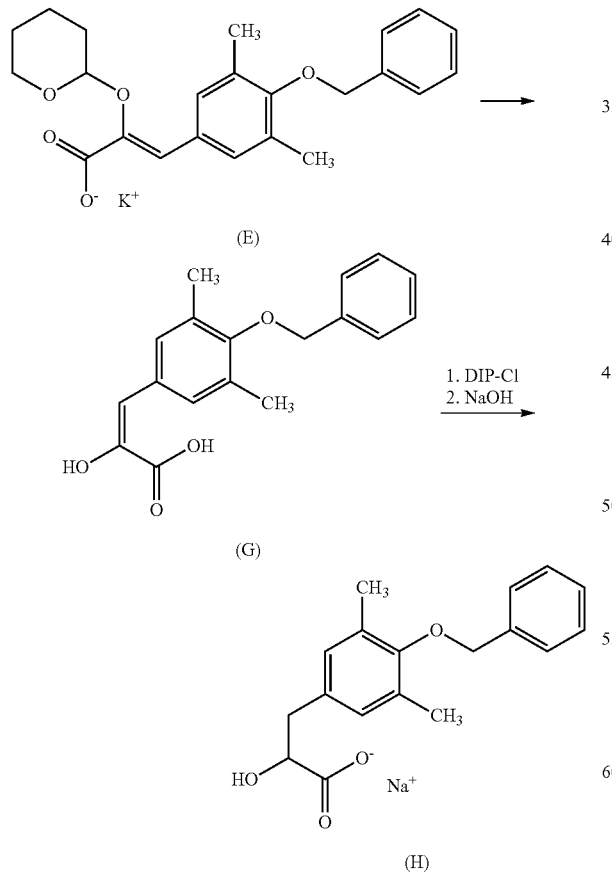

48.00 kg (114.14 mol) (3Z)-3-(4-benzyloxy-3,5-dimethyl-phenyl)-2-tetrahydro-pyran-2-yloxy)-acrylic acid monopotassium salt (E) were suspended in 288.0 L toluene. At 0 to 5° C., 23.04 kg (239.69 mol) methanesulphonic acid were added. The suspension obtained was stirred for 30 minutes at −5° C. After the reaction was complete 26.56 kg (262.52 mol) of triethylamine were added. The suspension was then combined with 84.49 kg (171.21 mol) with diisopinocampheyl borochloride (65% in heptane) at a temperature of −5° C. Then the temperature of the reaction mixture was allowed to rise to 20° C. within 1 hour and 192.0 L water were added dropwise. The temperature of the 2-phase mixture was adjusted to 25° C. and the aqueous phase was separated off. The organic phase was combined with 308.0 L water and 10.04 kg (125.55 mol) sodium hydroxide solution (50%). The 2-phase mixture was heated to 70° C. and the aqueous phase (product phase) was separated off. Then a further 144 L of water were added and 48.0 L of solvent were distilled off in vacuo. The solution was cooled to 45° C. and inoculated. Then it was cooled further to 20° C. After 30 minutes stirring at 20° C. the product obtained was centrifuged off and dried.

Yield: 23.9 kg (65% of theory)
ee value: 99.6%
Chemical purity (HPLC): 99.9%

Example 4.3

(αR)-α-hydroxy-3,5-dimethyl-4-(phenylmethoxy)-phenylpropionic acid-monosodium salt (H)

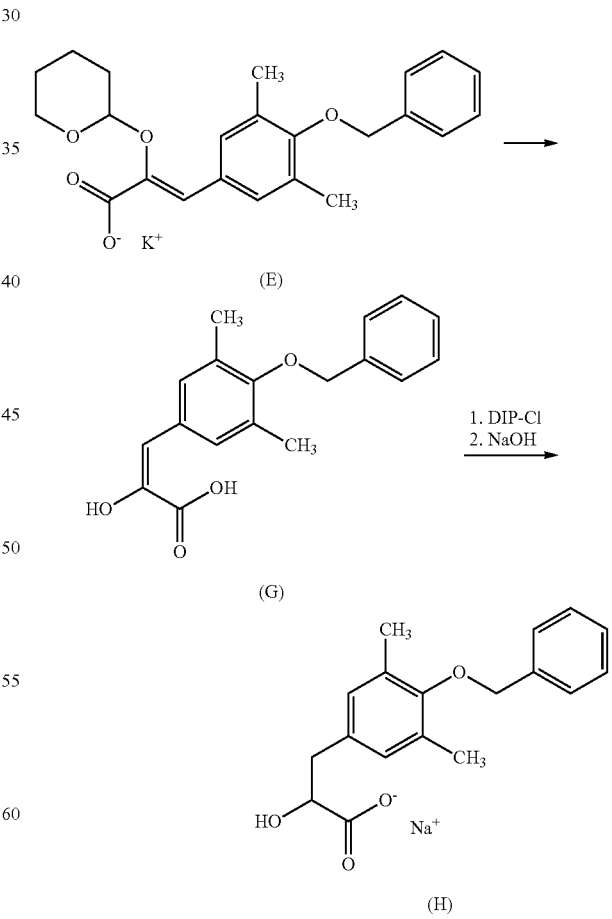

61.9 kg (147.4 mol) (3Z)-3-(4-benzyloxy-3,5-dimethyl-phenyl)-2-tetrahydro-pyran-2-yloxy)-acrylic acid-monopotassium salt (E) were suspended in 300 kg toluene and at 0 C 27.0 L (189 mol) dioxanic HCl (7.0 mol) were metered in and 22 kg of toluene were then added. The resulting suspension was stirred at the same temperature for 30 minutes. The suspension was then combined with 87.3 kg (177.3 mol) diisopinocampheylborochloride (65% in heptane) at a temperature of 20° C. within 30 min and then stirred for another 30 min at the same temperature. The resulting solution was then extracted with 309 L water at the same temperature. The organic phase was combined with 319 L water and 14.4 kg (162 mol) sodium hydroxide solution (45%). The 2-phase mixture was heated to 70° C. and the aqueous phase (product phase) was separated off. After dilution of this phase with 124 L water the solution was cooled to 40° C., inoculated with 240 g (H), cooled to 25° C. and stirred for a minimum of 30 min. The product obtained was filtered off, washed with 20 ml of water and dried.

Yield: 26.7 kg (56% of theory)
ee value: 98.6%
Chemical purity (HPLC): 99.9%

Example 4.4

(αR)-α-hydroxy-3,5-dimethyl-4-(phenylmethoxy)-phenylpropionic acid-monosodium salt (H)

added. The suspension obtained was stirred at 5-10° C. for 30 minutes. The suspension was then combined with 28.2 g (57.2 mmol) diisopinocampheylborochloride (65% in heptane) at a temperature of 20° C. and then stirred for 30 min at the same temperature. The resulting solution was then extracted with 60 mL water at the same temperature. The organic phase was combined with 60 mL water and 4.2 g (52.5 mmol) sodium hydroxide solution (50%). The 2-phase mixture was heated to 70° C. and the aqueous phase (product phase) was separated off. After dilution with 80 mL water the solution was cooled to 40° C., inoculated and stirred for a further 10 min at inoculation temperature. Then it was cooled further to 20° C. and stirred for 2 h. The product obtained was filtered off, washed with 20 ml of water and dried.

Yield: 9.2 g (60% of theory)
ee value: >99.9%
Chemical purity (HPLC): 99.9%

Example 5.1

Ethyl(1R)-4-(1,2,4,5-tetrahydro-2-oxo-3H-1,3-benzodiazepin-3-yl)-1-carboxy-2-[3,5-dimethyl-4-(phenylmethoxy)phenyl]-1-piperidinecarboxylate (J)

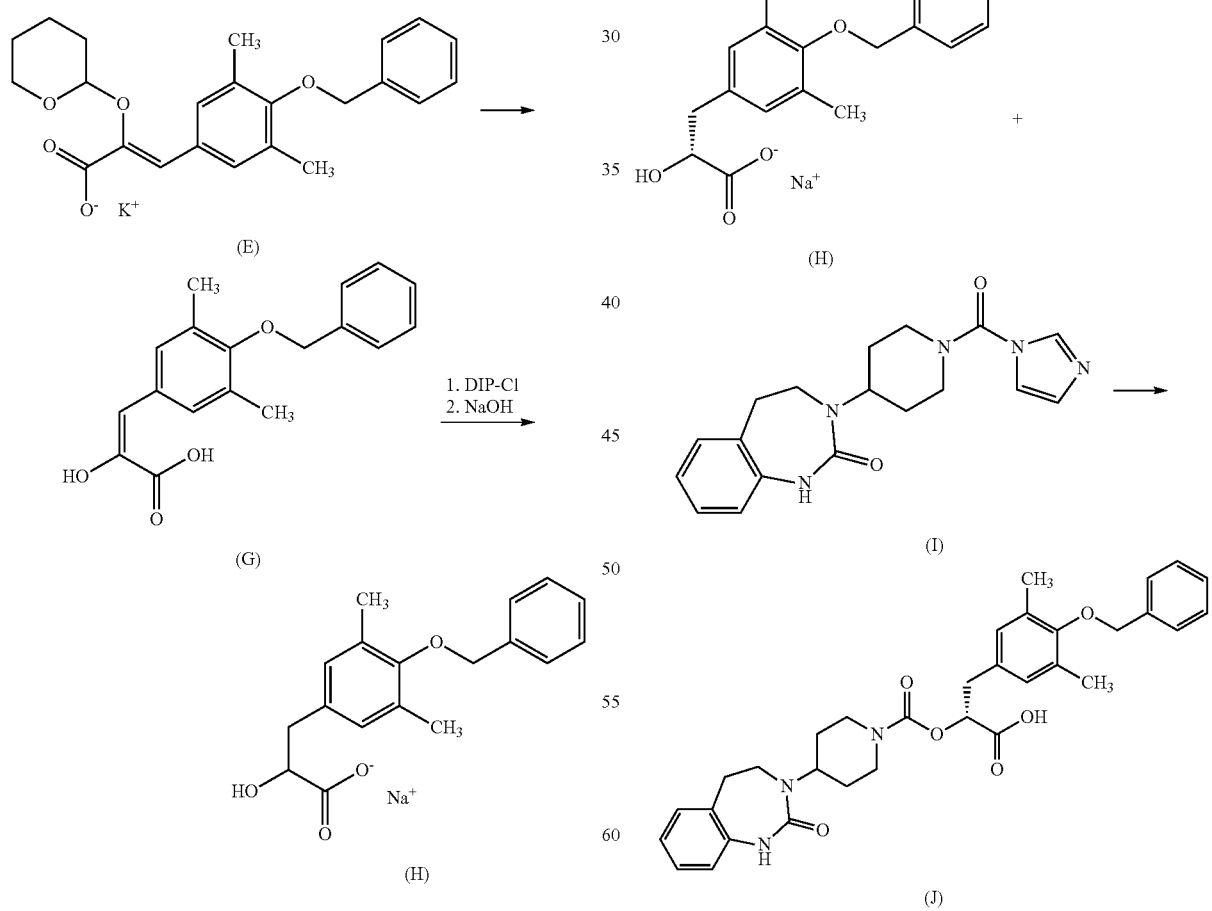

20 g (47.6 mmol) (3Z)-3-(4-benzyloxy-3,5-dimethyl-phenyl)-2-tetrahydro-pyran-2-yloxy)-acrylic acid-monopotassium salt (E) were suspended in 60 mL toluene. At 0 to 5° C., 12 mL (144.9 mmol) 37% aqueous hydrochloric acid were 10.00 kg (31.02 mol)) (αR)-α-hydroxy-3,5-dimethyl-4-(phenylmethoxy)-phenylpropionic acid monosodium salt (H) were taken, 12.11 kg (35.68 mol) 1-(1H-imidazol-1-ylcarbonyl)-4-(1,2,4,5-tetrahydro-2-oxo-3H-1,3-benzodiazepin-3-yl)-piperidine (I) were added and this mixture was suspended in 160.0 L tert-amylalcohol. 30.0 L solvent were then distilled off at normal pressure. Then 15.96 kg (34.13 mol) potassium-tert-butoxide solution in tetrahydrofuran were added to the reaction mixture at 82° C. and rinsed with 10.0 L tert-amylalcohol. After one hour's stirring at 82° C., 16.59 kg (136.51 mol) hydrochloric acid (30%) were added. After crystallisation started 23 L water were run in and the suspension was cooled to 22° C. Then the suspension was stirred for 16 hours at 22° C., the product obtained was removed by centrifuging and dried.

Yield: 17.70 kg (93% of theory)
ee value: 99.9%
Chemical purity (HPLC): 98.7%
Melting point: 132° C.

Example 5.2

Ethyl(1R)-4-(1,2,4,5-tetrahydro-2-oxo-3H-1,3-benzodiazepin-3-yl)-1-carboxy-2-[3,5-dimethyl-4-(phenylmethoxy)phenyl]-1-piperidinecarboxylate (J)

suspended in 510.0 L of tert-amylalcohol. 120.0 L solvent were then distilled off at normal pressure. Then 57.44 kg (102.38 mol) potassium-tert-butoxide solution in tetrahydrofuran were added to the reaction mixture at 82° C. and rinsed with 30.0 L tert-amylalcohol. After 1.5 hours stirring at 82° C., 49.77 kg (409.52 mol) hydrochloric acid (30%) were added. After crystallisation started 69.0 L water were allowed to run in and the suspension cooled to 22° C. Then the suspension was stirred for at least 2 hours at 22° C., the product obtained was removed by centrifuging and dried.

Yield: 47.88 kg (90% of theory)
ee value: 99.9%
Chemical purity (HPLC): 98.7%
melting point: 132° C.

Example 5.3

Ethyl(1R)-4-(1,2,4,5-tetrahydro-2-oxo-3H-1,3-benzodiazepin-3-yl)-1-carboxy-2-[3,5-dimethyl-4-(phenylmethoxy)phenyl]-1-piperidinecarboxylate (J)

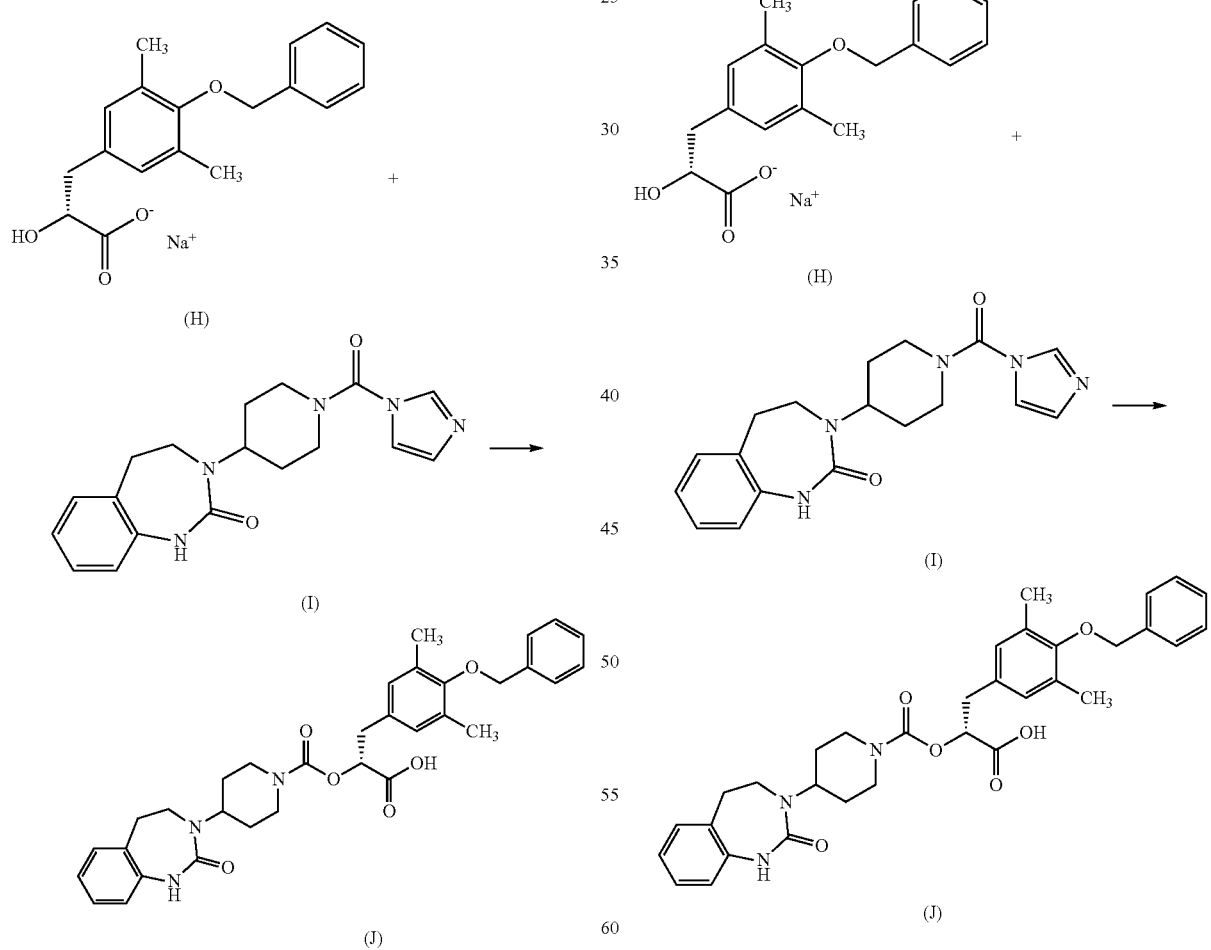

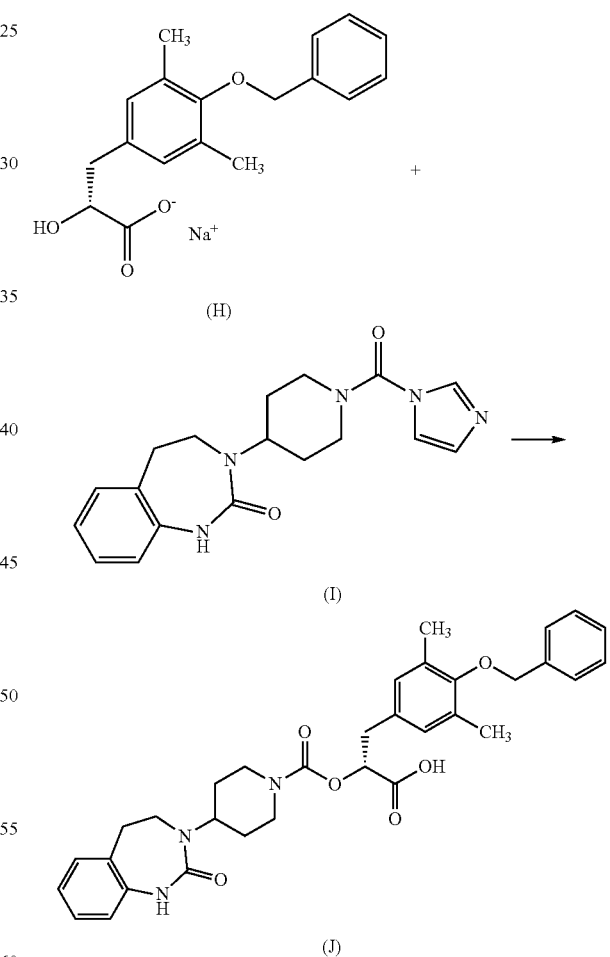

30.00 kg (93.07 mol)) (αR)-α-hydroxy-3,5-dimethyl-4-(phenylmethoxy)-phenylpropionic acid monosodium salt (H) were taken, 33.17 kg (97.72 mol) 1-(1H-imidazol-1-yl-carbonyl)-4-(1,2,4,5-tetrahydro-2-oxo-3H-1,3-benzodiazepin-3-yl)-piperidine (I) were added and this mixture was 55.4 kg (172.0 mol)) (αR)-α-hydroxy-3,5-dimethyl-4-(phenylmethoxy)-phenylpropionic acid monosodium salt (H) were taken, 64.2 kg (189.4 mol) 1-(1H-imidazol-1-yl-carbonyl)-4-(1,2,4,5-tetrahydro-2-oxo-3H-1,3-benzodiazepin-3-yl)-piperidine (I) were added and this mixture was suspended in 149 kg N,N-dimethylformamide. Then at 70°

C., 111 kg (198.2 mol) of a 20% potassium-tert-butoxide solution in tetrahydrofuran were added to the reaction mixture. The resulting solution was stirred for 30 min and then diluted successively with 23 kg N,N-dimethylformamide, 192 L water and 100 kg isopropanol. Then 66.2 kg (653.6 mol) hydrochloric acid (36%) were added at 65° C. After inoculation at the same temperature the mixture was cooled to 20° C. stepwise within 2.5 h and stirred for a further 60 min. The product obtained was centrifuged off and dried.

Yield: 96.6 kg (98% of theory)
ee value: 99.7%
Chemical purity (HPLC): 99.5%

Example 6.1

4-[1-(phenylmethyl)-4-piperidinyl]-morpholine-dihydrochloride (M)

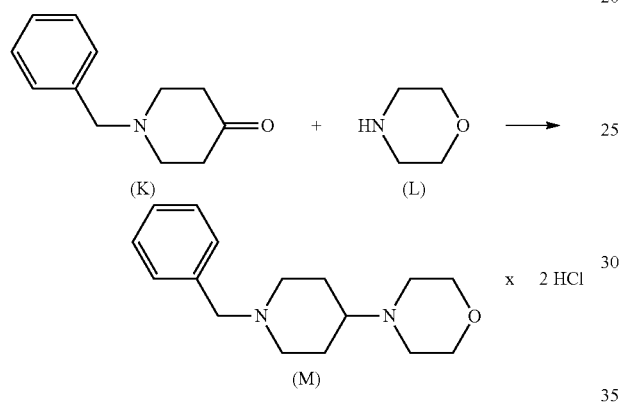

10.00 kg (52.84 mol) 1-benzylpiperidone (K) were taken and 9.21 kg (105.68 mol) morpholine (L) and 30.0 L isopropylacetate were added. Then the reaction mixture obtained was heated to reflux temperature (95° C.) using the water separator and stirred until no more water separated off. Then the mixture was hydrogenated at 4 bar and at an internal temperature of 60° C. in the presence of 0.50 kg Raney nickel catalyst. Then the solvent was completely distilled off in vacuo. Then 45.0 L ethanol were added and 10.87 kg (116.25 mol) ethanolic 10-mol hydrochloric acid were metered in. The resulting suspension was cooled to 20° C. and stirred for 30 minutes at 20° C. The product was centrifuged off and dried.

Yield: 15.1 kg (86% of theory)
Chemical purity (GC): 99.7%

Example 6.2

4-[1-(phenylmethyl)-4-piperidinyl]-morpholine-dihydrochloride (M)

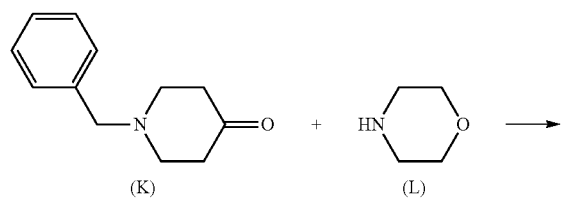

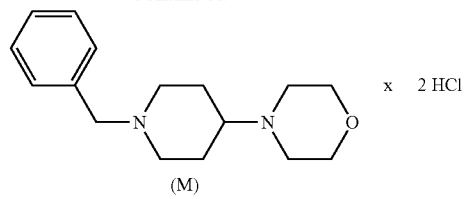

10.00 kg (52.84 mol) 1-benzylpiperidone (K) were taken and 9.21 kg (105.68 mol) morpholine (L) as well as 50.0 L toluene were added. Then the reaction mixture obtained was heated to reflux temperature using the water separator (110° C.) and stirred until no more water separated off. Then the mixture was hydrogenated at 4 bar and an internal temperature of 60° C. in the presence of 0.50 kg Raney nickel catalyst in 6 L ethanol. The catalyst was separated off and washed with 20 L ethanol. Then the solvent was distilled off completely in vacuo. Then 80.0 L ethanol were added and at 50° C. 16.05 kg (132.10 mol) hydrochloric acid (30%) were metered in. The resulting suspension was cooled to 20° C. and stirred for 30 minutes at 20° C. The product was centrifuged off and dried.

Yield: 15.5 kg (88% of theory)
Chemical purity (GC): 99.9%

Example 7

4-(4-piperidinyl)-morpholine (N)

10.00 kg (30.00 mol) 4-[1-(phenylmethyl)-4-piperidinyl]-morpholine-dihydrochloride (M) were suspended in 50.0 L tert-butanol and 10.0 L water and heated to 45° C. At 45° C. a solution of 10.37 kg (75.01 mol) potassium carbonate in 24.0 L water was metered in. Then the aqueous phase was separated off at 45° C. and 20.0 L solvent were distilled off in vacuo. The mixture was then hydrogenated at a pressure of 4 bar and an internal temperature of 60° C. until no further uptake of hydrogen could be detected. After the reaction was complete, the catalyst was filtered off and the residue was washed with 20.0 L tert-butanol.

The hydrogenating solution obtained was then transferred into a reactor and the solvent was distilled off completely in vacuo. An oil is left behind which crystallises after a short time.

Yield: 5.53 kg (88% of theory)
Melting point: 40.6° C.

Example 8

4-(4-piperidinyl)-morpholine hydrochloride (O)

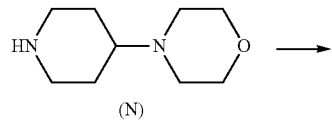

(N)

↓

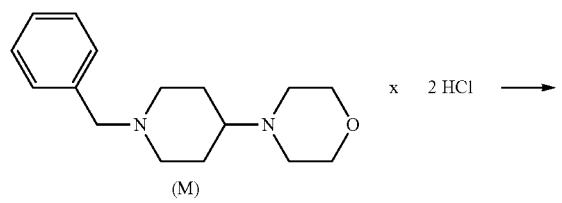

10.00 kg (58.74 mol) 4-(4-piperidinyl)-morpholine (N) were placed in 100.0 L ethanol and heated to 50° C. At 50° C., 12.15 kg (123.35 mol) conc. hydrochloric acid (37%) were metered in. The resulting suspension was cooled to 20° C. and stirred for 30 minutes at 20° C. The product was centrifuged off and dried.

Yield: 11.46 kg (80% of theory)

Example 9

4-(4-piperidinyl)-morpholine hydrochloride (O)

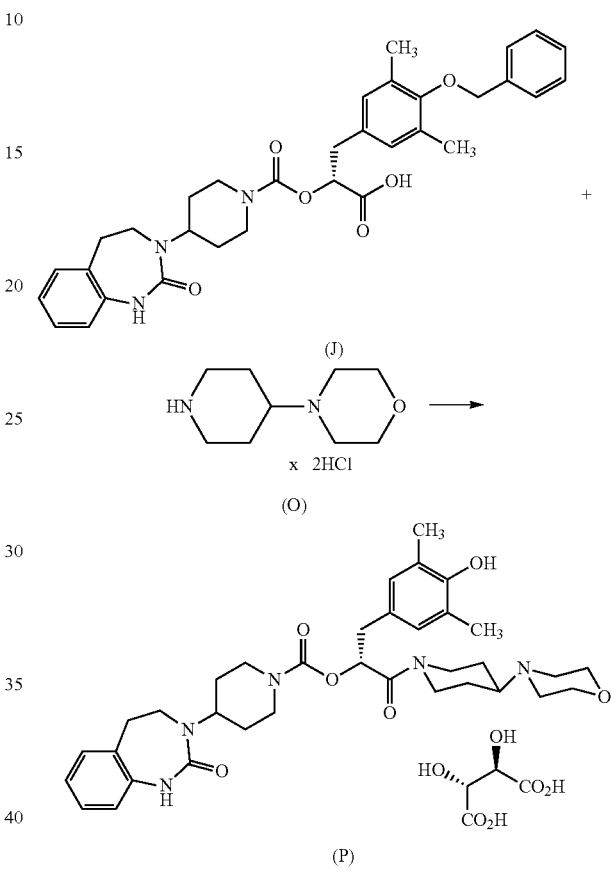

30.00 kg (90.01 mol) 4-[1-(phenylmethyl)-4-piperidinyl]-morpholine-dihydrochloride (M) were dissolved in 67.5 L methanol and 20.0 L water. Then the mixture was hydrogenated at a pressure of 4 bar and an internal temperature of 50° C. in the presence of 1.80 kg palladium on charcoal until no further uptake of hydrogen could be detected. After the reaction had ended the catalyst was filtered off and washed with a mixture of 18.0 L methanol and 2.0 L water. The hydrogenation solution obtained was then transferred into a reactor and heated to 60° C. At 60° C. 540.0 L ethanol were metered in. The resulting suspension was cooled to 5° C. The product was centrifuged off and dried.

Yield: 19.69 kg (90% of theory)

Chemical purity (GC): 99.8%

Example 10.1

2-oxoethyl(1R)-4-(1,2,4,5-tetrahydro-2-oxo-3H-1,3-benzodiazepin-3-yl)-1-[[3,5-dimethyl-4-hydroxy)phenyl]methyl]-2-[4-(4-morpholinyl)-1-piperidinyl]-1-piperidinecarboxylate tartrate (P)

10.00 kg (17.49 mol) ethyl (1R)-4-(1,2,4,5-tetrahydro-2-oxo-3H-1,3-benzodiazepin-3-yl)-1-carboxy-2-[3,5-dimethyl-4-(phenylmethoxy)phenyl]-1-piperidinecarboxylate (J) were taken and 5.10 kg (20.99 mol) 4-(4-piperidinyl)-morpholine-dihydrochloride (O) and 85.0 L ethyl acetate were added thereto. At 20° C., 8.85 kg (87.45 mol) triethylamine were added to the reaction mixture obtained and then the mixture was rinsed with 5.0 L ethyl acetate. Within 30 minutes, 17.81 kg (27.99 mol) 50% propanephosphonic anhydride were added dropwise. After another 30 minutes reaction time, 25.0 L water were added. The aqueous phase was separated off and a solution of 3.63 kg (26.24 mol) potassium carbonate in 25.0 L water was added. The aqueous phase was separated off and 85.0 L solvent were distilled off at normal pressure. Then 118.0 L ethanol and 0.65 kg palladium/charcoal (10%) were added. The mixture was then hydrogenated at a pressure of 3 bar and an internal temperature of 40° C. until no further uptake of hydrogen could be detected. Once the reaction was complete, the catalyst was filtered off and the residue was washed with 20.0 L ethanol. At normal pressure 43.0 L solvent were distilled off and then 35.0 L isopropylalcohol were added at 75° C. The solution was filtered clear through a pressure filter, rinsed with 10.0 L isopropylalcohol and the reaction mixture was then cooled to 65° C. The solution was combined with 10 g seed crystals. Then a solution of 2.89 kg (19.24 mol) L (+)-tartaric acid in 3.0 L water was added and the mixture was rinsed with 5.0 L isopropylalcohol. After 1 hour's stirring at 65° C. the suspension was cooled to ambient temperature, the product was filtered and dried.

Yield: 10.97 kg (80% of theory)
Chemical purity (HPLC): 99.4%
ee value: 99.6%
Melting point: 198° C.

Example 10.2

2-oxoethyl(1R)-4-(1,2,4,5-tetrahydro-2-oxo-3H-1,3-benzodiazepin-3-yl)-1-[[3,5-dimethyl-4-hydroxy)phenyl]methyl]-2-[4-(4-morpholinyl)-1-piperidinyl]-1-piperidine carboxylate-tartrate (P)

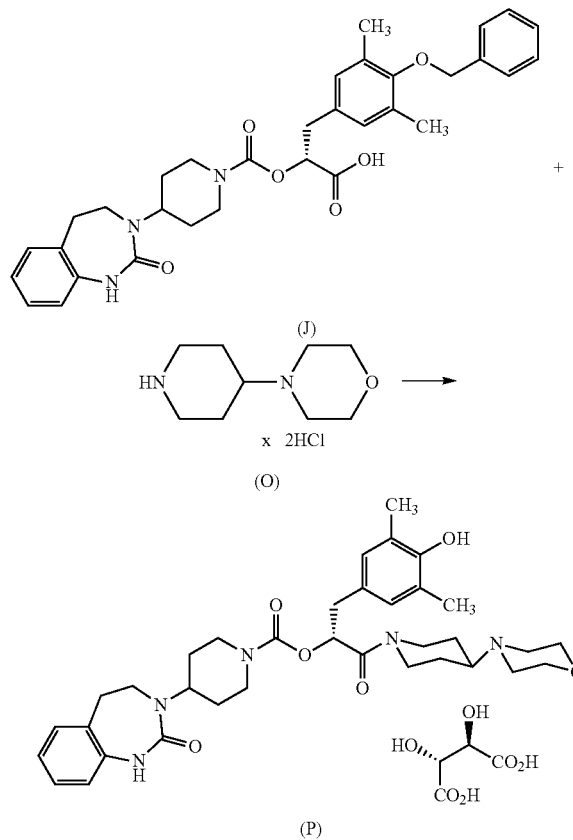

30.00 kg (52.48 mol) ethyl (1R)-4-(1,2,4,5-tetrahydro-2-oxo-3H-1,3-benzodiazepin-3-yl)-1-carboxy-2-[3,5-dimethyl-4-(phenylmethoxy)phenyl]-1-piperidinecarboxylate (J) were taken and 15.31 kg (62.97 mol) 4-(4-piperidinyl)-morpholine-dihydrochloride (O) and 210.0 L ethyl acetate were added thereto. At 40° C., 26.55 kg (262.39 mol) triethylamine were added to the reaction mixture obtained and then it was rinsed with 15.0 L of ethyl acetate. Within 30 minutes, 53.43 kg (83.97 mol) 50% propanephosphonic anhydride were added dropwise at 40° C. After another 2 hours' reaction time 60.0 L water were added. The aqueous phase was separated off and a solution of 10.88 kg (78.72 mol) potassium carbonate in 60.0 L water was added. The aqueous phase was separated off and the organic phase was again washed with 60 L water. Then 210.0 L solvent was distilled off in vacuo. Then 90.0 L ethanol and 1.95 kg palladium/charcoal (10%) were added. Then the mixture was hydrogenated at a pressure of 3 bar and an internal temperature of 40° C. until no further uptake of hydrogen could be detected. After the reaction was complete the catalyst was filtered off and washed with 35.0 L isopropanol.

The solution was filtered clear through a pressure filter, rinsed with 10.0 L isopropylalcohol and the reaction mixture was then heated to 65° C. The solution was combined with 30 g of seed crystals. Then a solution of 9.06 kg (60.35 mol) L (+)-tartaric acid in 9.0 L water was added and the mixture was rinsed with 7.5 L isopropylalcohol. After 1 hour's stirring at 65° C. the suspension was cooled to 5° C. within 1.5 hours, stirred for 1 hour, the product was filtered and dried.

Yield: 34.80 kg (85% of theory)
Chemical purity (HPLC): 99.4%
ee value: 99.6%
melting point: 198° C.

Example 10.3

2-oxoethyl(1R)-4-(1,2,4,5-tetrahydro-2-oxo-3H-1,3-benzodiazepin-3-yl)-1-[[3,5-dimethyl-4-hydroxy)phenyl]methyl]-2-[4-(4-morpholinyl)-1-piperidinyl]-1-piperidinecarboxylate tartrate (P)

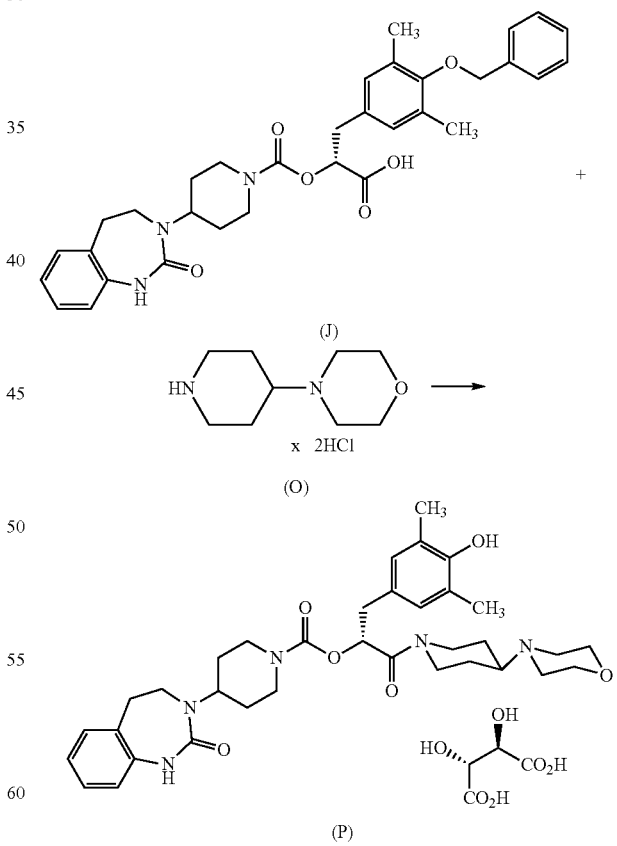

32.6 kg (133.9 mol) 4-(4-piperidinyl)-morpholine-dihydrochloride (O) were placed in 290 kg toluene, combined with 56.4 kg (557.4 mol) triethylamine and the mixture was stirred at 85° C. for 60 min. The suspension was cooled to 30°

C. and combined with 61.2 kg (107.1 mol) ethyl (1R)-4-(1,2,4,5-tetrahydro-2-oxo-3H-1,3-benzodiazepin-3-yl)-1-carboxy-2-[3,5-dimethyl-4-(phenylmethoxy)phenyl]-1-piperidinecarboxylate (J). Then 105.4 kg (165.6 mol) 50% propanephosphonic anhydride in ethyl acetate were added dropwise within 30 minutes at 40° C. and the mixture was rinsed with 26 kg toluene. After another 3 hours' reaction time 245 L water and 98 kg 2-butanol were added successively. The aqueous phase was separated off at 50° C. and the organic phase was combined with 18.4 kg (183.6 mol) potassium hydrogen carbonate and 245 L water. After phase separation again at 50° C. and further extraction with 184 L water the organic phase was combined with 3.1 kg of Norit SX Ultra and 33 L ethanol and then filtered. 33 L ethanol and 3.1 kg palladium/charcoal (10%) were added to the solution. Then the mixture was hydrogenated at a pressure of 4 bar and an internal temperature of max. 50° C. until no further uptake of hydrogen could be detected. After the reaction had ended the catalyst was filtered off and washed with 44 L ethanol. The solution was concentrated at 60° C. in vacuo down to one-third of the original volume, combined with 98 kg ethanol and filtered clear through a pressure filter. The filtrate was diluted at 65° C. with 242 kg of isopropylalcohol. Then a solution of 18.7 kg (124.5 mol) L (+)-tartaric acid in 22 L water was added and the mixture was rinsed with 49 kg ethanol. The reaction mixture was inoculated at 65° C., stirred for 45 min at this temperature and then stirred for a further 2 h at 20° C. Finally the product was filtered, dried and equilibrated to a defined water content using a moist current of nitrogen.

Yield: 80.8 kg (94% of theory)

Chemical purity (HPLC): 99.7% ee value: >99.5%

Example 11

(3z)-3-(4-tert-butyloxycarbonyloxy-3,5-dimethyl-phenyl)-2-tetrahydro-pyran-2-yloxy)-acrylic acid-monodicyclohexylamine salt (S)

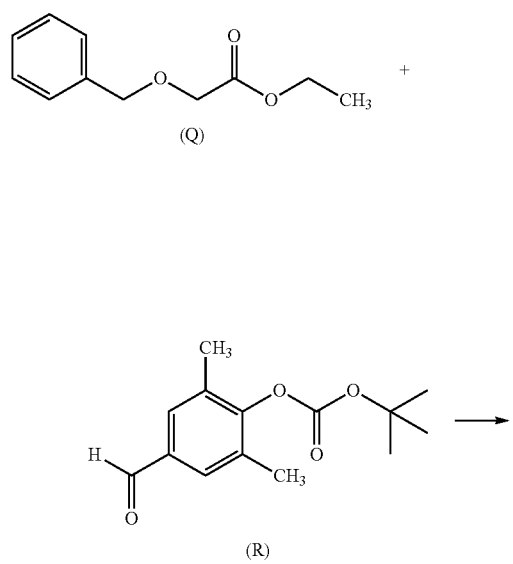

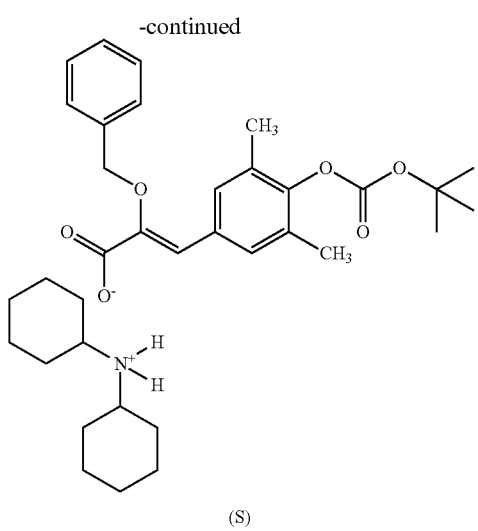

20.00 g (79.91 mmol) 4-tert-butyloxycarbonyloxy-3,5-dimethylbenzaldehyde (R) were dissolved in 120.0 ml of 2-methyltetrahydrofuran and 31.04 g (194.23 mmol) ethyl benzyloxy-acetate (Q) were added. At 20° C., 26.9 g (95.90 mol) potassium-tert-amylate (45% in tetrahydrofuran) were added dropwise. Then the reaction mixture obtained was stirred for 2 hours at 20° C. and once the reaction was complete the mixture was combined with 30 ml of water and 16.0 g sodium hydroxide solution (50%) (199.8 mmol). The reaction mixture was heated to reflux temperature and stirred for 1 hour. After neutralisation with acetic acid and phase separation the organic phase was evaporated down in vacuo. The residue was combined with 80 ml of toluene and 250 ml n-heptane. After the addition of 30.0 g (165.45 mmol) dicyclohexylamine the suspension obtained was stirred for 20 hours at ambient temperature. Then the product was filtered and dried.

Yield: 11.47 g (24.8% of theory)

Melting point: 140° C.

The invention claimed is:

1. A process for preparing a compound of the formula I

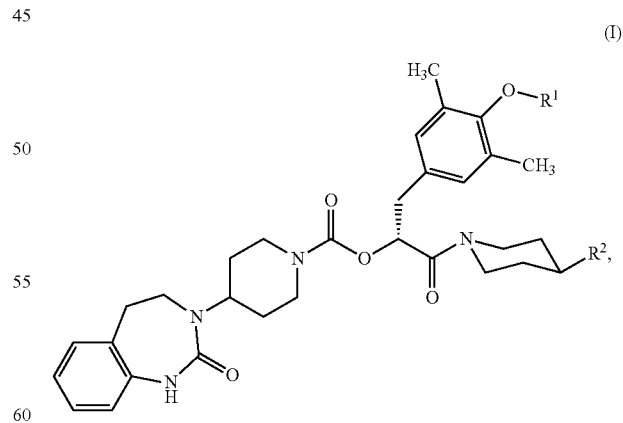

wherein:
$R^1$ denotes H, $C_{1-3}$-alkyl, C(O)—O-benzyl, C(O)—O-tert-butyl or benzyl, and
$R^2$ denotes a secondary amine —$NR^{2.1}R^{2.2}$, wherein $R^{2.1}$ and $R^{2.2}$ independently of one another may be selected from among $C_{1-3}$-alkyl and benzyl, or the group —NR$^{2.1}$R$^{2.2}$ together forms a cyclic amine which may be selected from among morpholin-4-yl, 1-methylpiperazin-4-yl, 1-benzylpiperazin-4-yl, 1-(C$_{1-3}$- alkylcarbonyl)-piperazin-4-yl, 1-(tert-butyloxy-carbonyl)-piperazin-4-yl, 1-(benzyloxycarbonyl)-piperazin-4-yl, piperidin-1-yl- and yrrolidin-1-yl, comprising the steps of:

(a) reacting an ethyl glycolate of the formula II

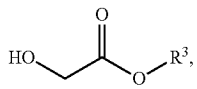
(II)

wherein R$^3$ denotes a C$_{1-6}$-alkyl group with a reagent in order to introduce a protective group, optionally in the presence of an acid and in a non-polar aprotic solvent, to form an ester of the formula III

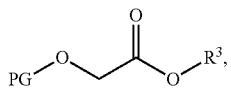
(III)

wherein

PG denotes a protective group, and

R$^3$ denotes a C$_{1-6}$-alkyl group;

(b) mixing the ester of the formula III obtained in step (a) with a solvent and reacting it in the presence of a strong base with a compound of the formula IV

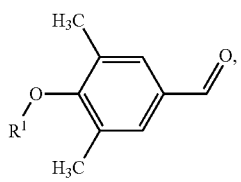
(IV)

wherein R$^1$ is as hereinbefore defined, to yield a compound of the formula V

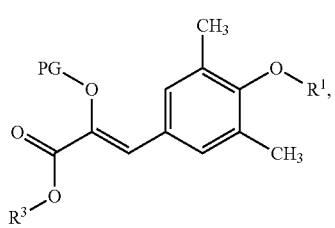
(V)

wherein PG, R$^1$ and R$^3$ are as hereinbefore defined;

(c) mixing the compound of formula V obtained in step (b) with a solvent and adding a strong base, to yield a compound of the formula VI

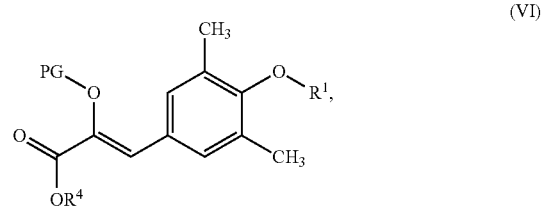
(VI)

wherein

PG denotes a protective group,

R$^1$ denotes H, C$_{1-3}$-alkyl, C(O)—O-benzyl, C(O)—O-tert-butyl or benzyl,

R$^4$ denotes a group H$_2$N$^+$(R$^{4.1}$)$_2$, HN$^+$(R$^{4.1}$)$_3$ or M$^+$, R$^{4.1}$ denotes benzyl, C$_{1-6}$-alkyl or C$_{3-6}$-cycloalkyl, wherein the groups R$^{4.1}$ may be identical or different, and M$^+$ denotes a metal cation selected from Na$^+$, K$^+$, and Li$^+$;

(d) optionally recrystallising the compound of formula VI obtained in step (c) from a polar solvent and isolating the compound obtained;

(e) mixing the compound of formula VI obtained in step (d) with a solvent and adding an acid at low temperature, to yield a compound of the formula VII

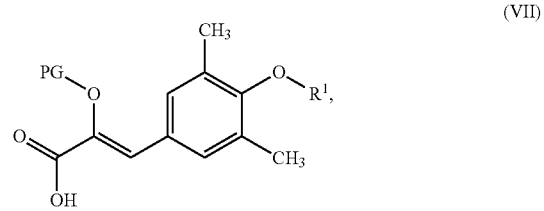
(VII)

wherein PG and R$^1$ are as hereinbefore defined;

(f) cleaving the protective group PG from the compound of the formula VII obtained in step (e), to yield a compound of the formula VIII

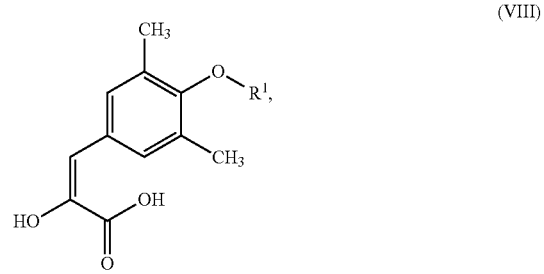
(VIII)

wherein R$^1$ is as hereinbefore defined;

(g) reducing the compound of formula VIII obtained in step (f) in the presence of a reducing agent and optionally also in the presence of a base, to form a compound of the formula IX

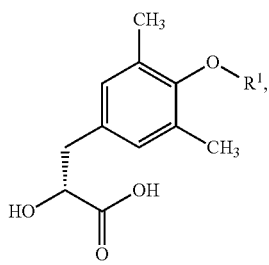
(IX)

wherein R¹ is as hereinbefore defined;
(h) isolating the compound of the formula IX, obtained in step (g), in the form of an alkali metal salt of the formula X

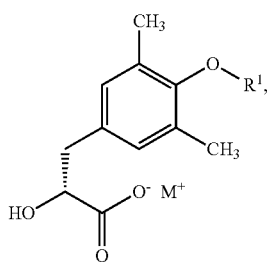
(X)

wherein R¹ is as hereinbefore defined and M⁺ denotes a metal cation selected from among Li⁺, Na⁺ and K⁺, by adding a corresponding alkaline solution of lithium hydroxide, sodium hydroxide or potassium hydroxide;
(i) coupling the compound of the formula X obtained in step (h) with a compound of the formula XI

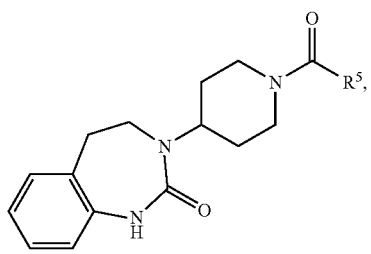
(XI)

wherein R⁵ denotes an imidazole or triazole group, which is attached via a nitrogen atom, to yield a product of the formula XII

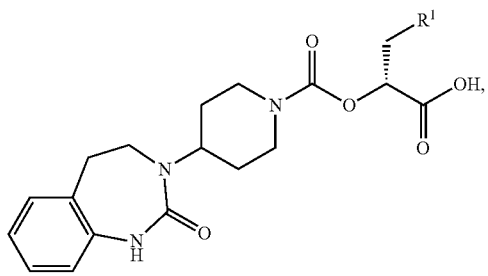
(XII)

wherein R¹ is as hereinbefore defined;
(j) reacting the product of the formula XII formed in step (i) with a compound of the formulae XIII

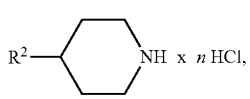
(XIII)

wherein R² is as hereinbefore defined and n denotes one of the numbers 0, 1, 2 or 3;
(k) in order to prepare a compound of the formula I wherein R¹ denotes a hydrogen atom, optionally subsequently cleaving any protective group present from a compound of the formula I wherein R¹ denotes C(O)—O-benzyl, C(O)—O-tert-butyl or a benzyl group; and
(l) optionally reacting a compound of the formula I obtained in step (k), wherein R¹ denotes a hydrogen atom, with a physiologically acceptable acid in a polar solvent to form a corresponding salt, crystallising out and isolating the corresponding salt.

2. The process according to claim 1, wherein R¹ denotes a hydrogen atom or a benzyl group.

3. The process according to claim 1, wherein R² denotes a secondary amine —NR²·¹R²·², wherein the group —NR²·¹R²·² together denotes morpholin-4-yl.

4. The process according to claim 1, wherein R³ denotes an ethyl group.

5. A compound of the formula V

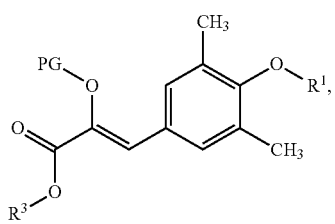
(V)

wherein:

PG denotes a protective group of the formula

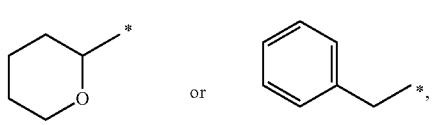

R¹ denotes H, C₁₋₃-alkyl, C(O)—O-benzyl, C(O)—O-tert-butyl or benzyl and

R³ denotes C₁₋₆-alkyl.

6. A compound of the formula V according to claim 5, selected from the group consisting of:

| No. | Structure |
|---|---|
| (1) | (Va) |
| (2) | (Vb) |
| (3) | (Vc), and |
| (4) | (Vd) |

7. The following compound of formula Va according to claim 5:

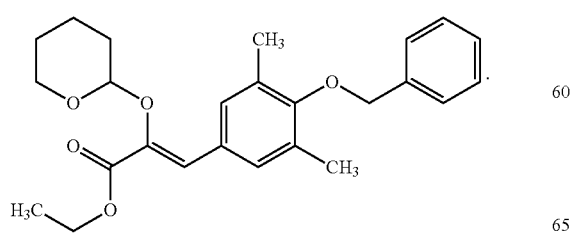

(Va)

8. A process for preparing a compound of the formula V

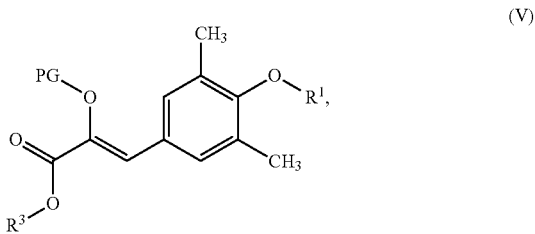

(V)

wherein:

PG denotes a protective group of the formula

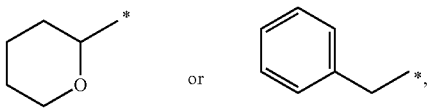

$R^1$ denotes H, $C_{1-3}$-alkyl, C(O)—O-benzyl, C(O)—O-tert-butyl or benzyl, and $R^3$ denotes $C_{1-6}$-alkyl, wherein, (a) a glycolic acid ester of the formula II

(II)

wherein $R^3$ denotes a $C_{1-6}$-alkyl group, is reacted with a reagent for introducing a protective group, optionally in the presence of an acid or a base, in a non-polar aprotic solvent, to form an ester of the formula III

(III)

wherein

PG denotes a protective group of the formula

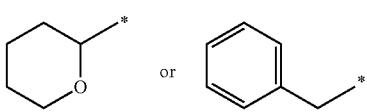

and

R³ denotes a $C_{1-6}$-alkyl group;

(b) an ester of the formula III obtained in step (a) is mixed with a solvent and reacted in the presence of a strong base with a compound of the formula IV

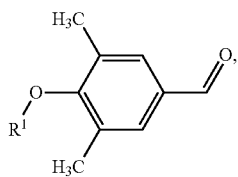

(IV)

wherein R¹ is as hereinbefore defined, to yield a compound of the formula V

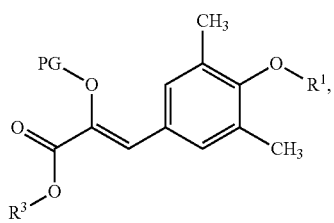

(V)

wherein PG, R¹ and R³ are as hereinbefore defined, and (c) the compound of the formula V obtained in step (b) is optionally recrystallised.

9. A compound of the formula VI

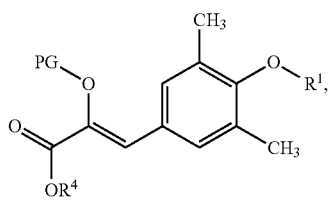

(VI)

wherein

PG denotes a protective group,

R¹ denotes H, $C_{1-3}$-alkyl, C(O)—O-benzyl, C(O)—O-tert-butyl or benzyl,

R⁴ denotes a group $H_2N^+(R^{4.1})_2$, $HN^+(R^{4.1})_3$ or $M^+$, $R^{4.1}$ denotes benzyl, $C_{1-6}$-alkyl or $C_{3-6}$-cycloalkyl and M⁺ denotes a metal cation selected from Na⁺, K⁺ and Li⁺.

10. A compound formula VI according to claim 9, selected from the group consisting of:

| No. | Structure |
|---|---|
| (1) | |
| (2) | 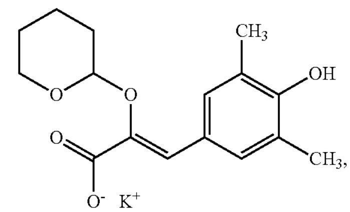 |
| (3) | 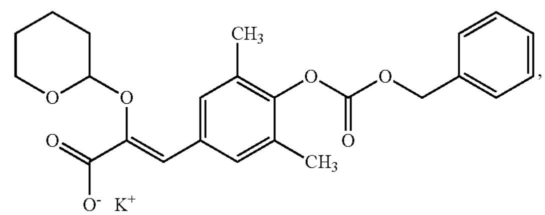 |
| (4) | 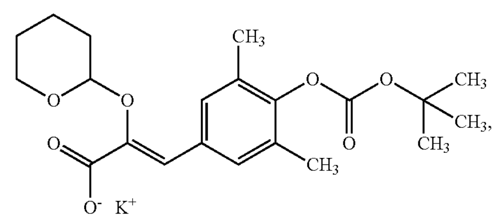 |
| (5) | 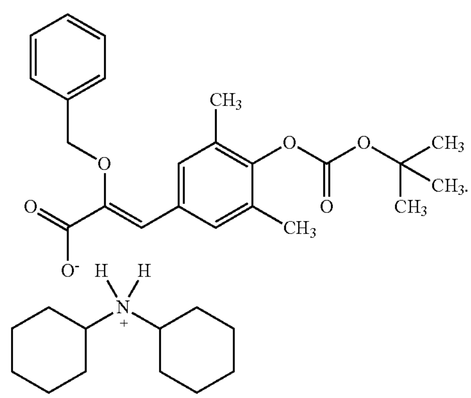 |

11. The following compound of formula VIa according to claim 9:

(VIa)

12. The following compound of formula VIe according to claim 9:

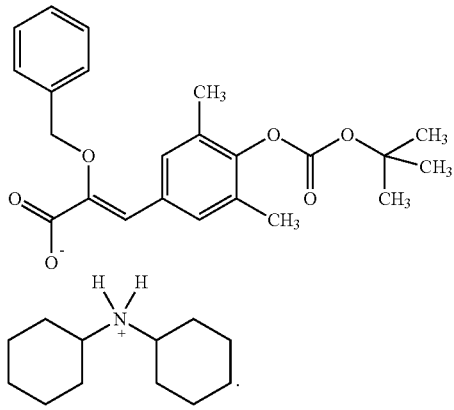

(VIe)

13. A process for preparing a compound of the formula VI

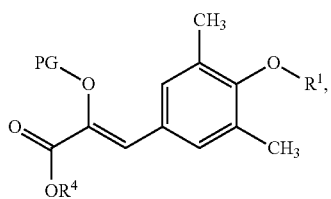

(VI)

wherein
PG denotes a protective group,
$R^1$ denotes H, $C_{1-3}$-alkyl, C(O)—O-benzyl, C(O)—O-tert-butyl or benzyl,
$R^4$ denotes a group $H_2N^+(R^{4.1})_2$, $HN^+(R^{4.1})_3$ or $M^+$,
$R^{4.1}$ denotes benzyl, $C_{1-6}$-alkyl or $C_{3-6}$-cycloalkyl and
$M^+$ denotes a metal cation selected from $Na^+$, $K^+$ and $Li^+$,
characterised in that
(a) a compound of the formula V

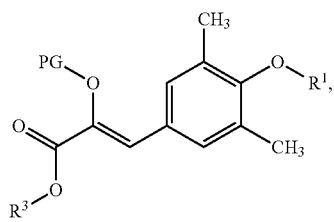

(V)

wherein PG, $R^1$ and $R^3$ are as hereinbefore defined, is mixed with a polar solvent and a strong inorganic base is added, to yield a compound of the formula IV

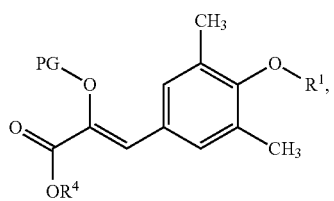

(VI)

wherein PG, $R^1$ and $R^4$ are as hereinbefore defined; and
(b) the compound of the formula VI obtained in step (a) is then isolated.

* * * * *